US008303535B2

(12) United States Patent
Both et al.

(10) Patent No.: US 8,303,535 B2
(45) Date of Patent: Nov. 6, 2012

(54) DELIVERY DEVICE FOR USE WITH A THERAPEUTIC DRUG

(75) Inventors: Marcel Both, Kirchlindach (CH); Kurt Friedli, Lyssach (CH); Heiner Kaufmann, Bern (CH); Juerg Liniger, Ostermundigen (CH); Fabio Oester, Zurich (CH); Allen Pearson, Wisow (GB); Daniel Peter, Niederwangen (CH); Dominik Scherrer, Vilters (CH); Simon Scheurer, Bern (CH); Oliver Shergold, Kirchberg (CH); Roger Siegenthaler, Muensingen (CH); Sofia Galbraith, Solothurn (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 13/062,957

(22) PCT Filed: Sep. 8, 2009

(86) PCT No.: PCT/EP2009/061592
§ 371 (c)(1),
(2), (4) Date: Mar. 9, 2011

(87) PCT Pub. No.: WO2010/029054
PCT Pub. Date: Mar. 18, 2010

(65) Prior Publication Data
US 2011/0166512 A1   Jul. 7, 2011

Related U.S. Application Data

(60) Provisional application No. 61/095,667, filed on Sep. 10, 2008.

(51) Int. Cl.
*A61M 37/00* (2006.01)

(52) U.S. Cl. .......................................... 604/67; 604/131
(58) Field of Classification Search .................... 604/67, 604/131
See application file for complete search history.

(56) References Cited

U.S. PATENT DOCUMENTS 5,531,683 A   7/1996   Kriesel et al.
(Continued)

FOREIGN PATENT DOCUMENTS
WO   2005077441 A2   8/2005

OTHER PUBLICATIONS

International Search Report and Written Opinion of the EPO as ISA as it relates to PCT/EP2009/061592 mailed Feb. 9, 2010.

*Primary Examiner* — Laura Bouchelle
(74) *Attorney, Agent, or Firm* — Dinsmore & Shohl LLP

(57) ABSTRACT

A compact and one time use, self-administration device (10) for administering medication is disclosed. The device includes a housing (12) having a start button (26), a status indicator (28), a window (30), and a surface removably attachable to a user. The device (10) has a cartridge holder (34) providing in an aseptic environment a cartridge (32) containing the medication. The cartridge (32) is viewable through the cartridge holder (34) and the window (30). An included drive unit (42) provides a movable plunger (126) that breaks through a sterile barrier (130) of the cartridge holder (34) to dispense the medication from the cartridge (32) to an hollow needle (38) for administering the medication into the user. The device (10) provides means (36, 44) for extending and retracting the hollow needle (38) and an electronic control unit (40) which controls the drive unit (42), the extending and retracting means (36, 44), and interfaces with the start button (26), the status indicator (28), and the body sensor (24) to automatically administer the medication.

44 Claims, 23 Drawing Sheets

U.S. PATENT DOCUMENTS

| | | |
|---|---|---|
| 5,860,957 A | 1/1999 | Jacobsen et al. |
| 5,919,167 A * | 7/1999 | Mulhauser et al. ............ 604/131 |
| 6,186,982 B1 * | 2/2001 | Gross et al. ................... 604/132 |
| 2003/0100888 A1 * | 5/2003 | Spinello ........................ 604/512 |
| 2007/0197968 A1 * | 8/2007 | Pongpairochana et al. .. 604/131 |
| 2008/0058732 A1 | 3/2008 | Harris |

* cited by examiner

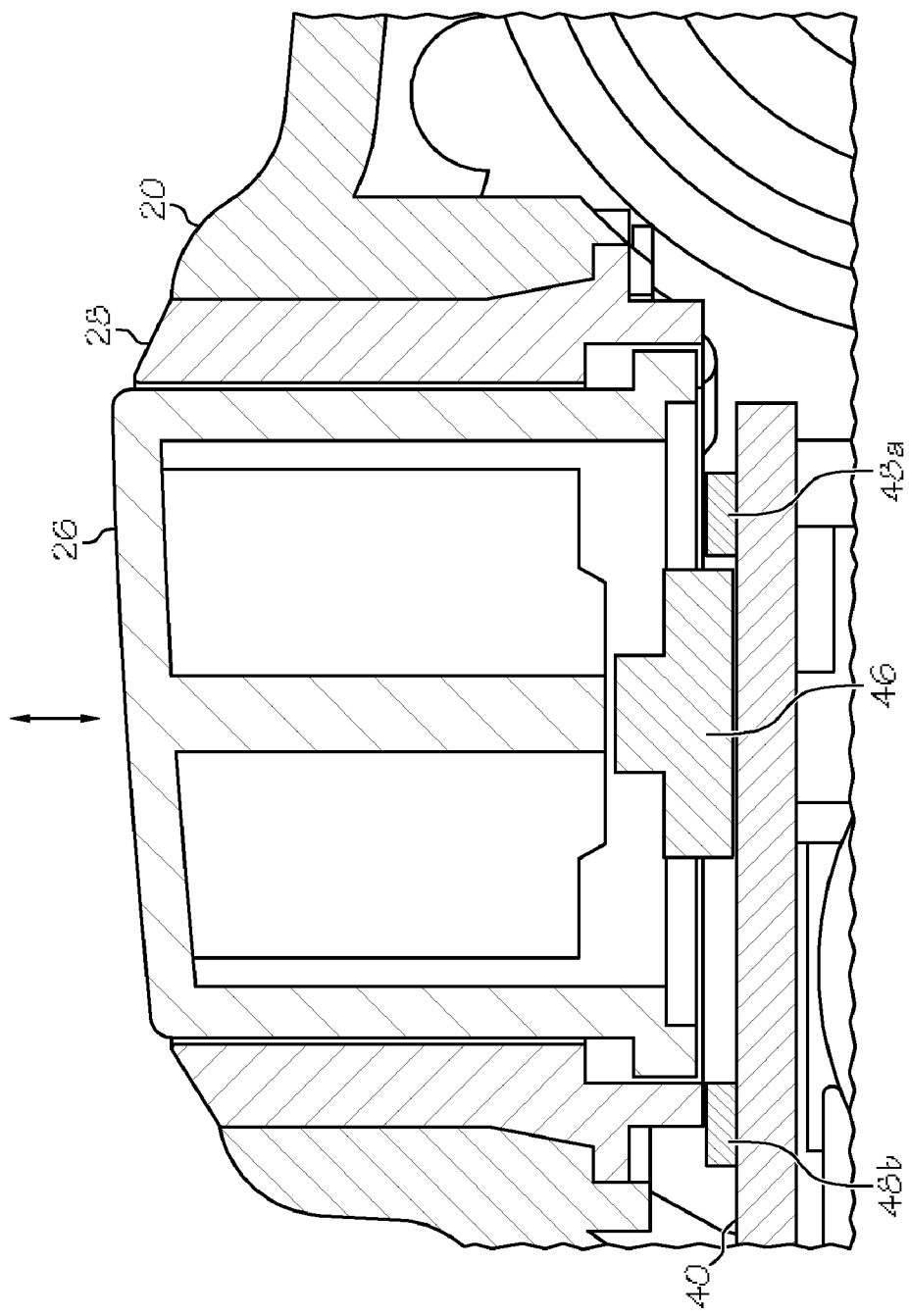

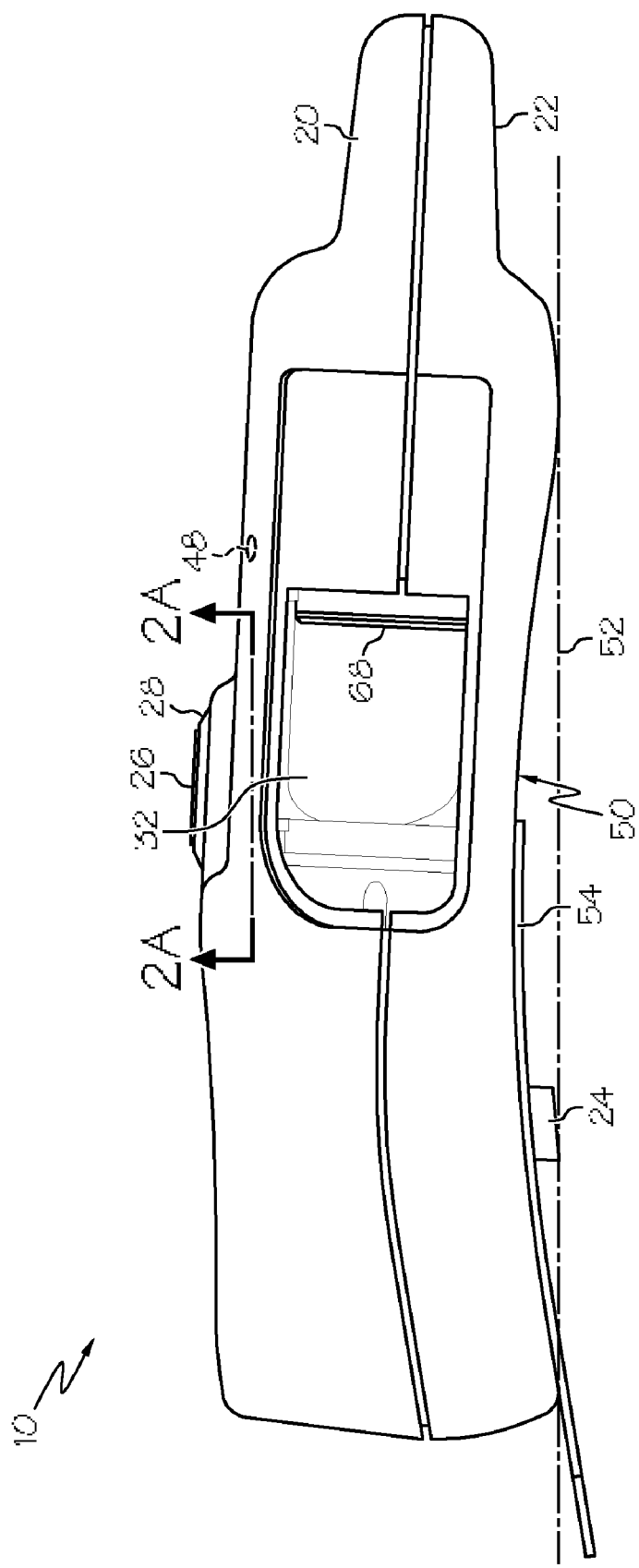

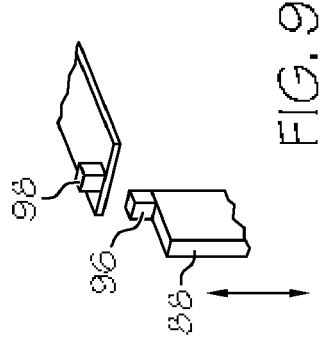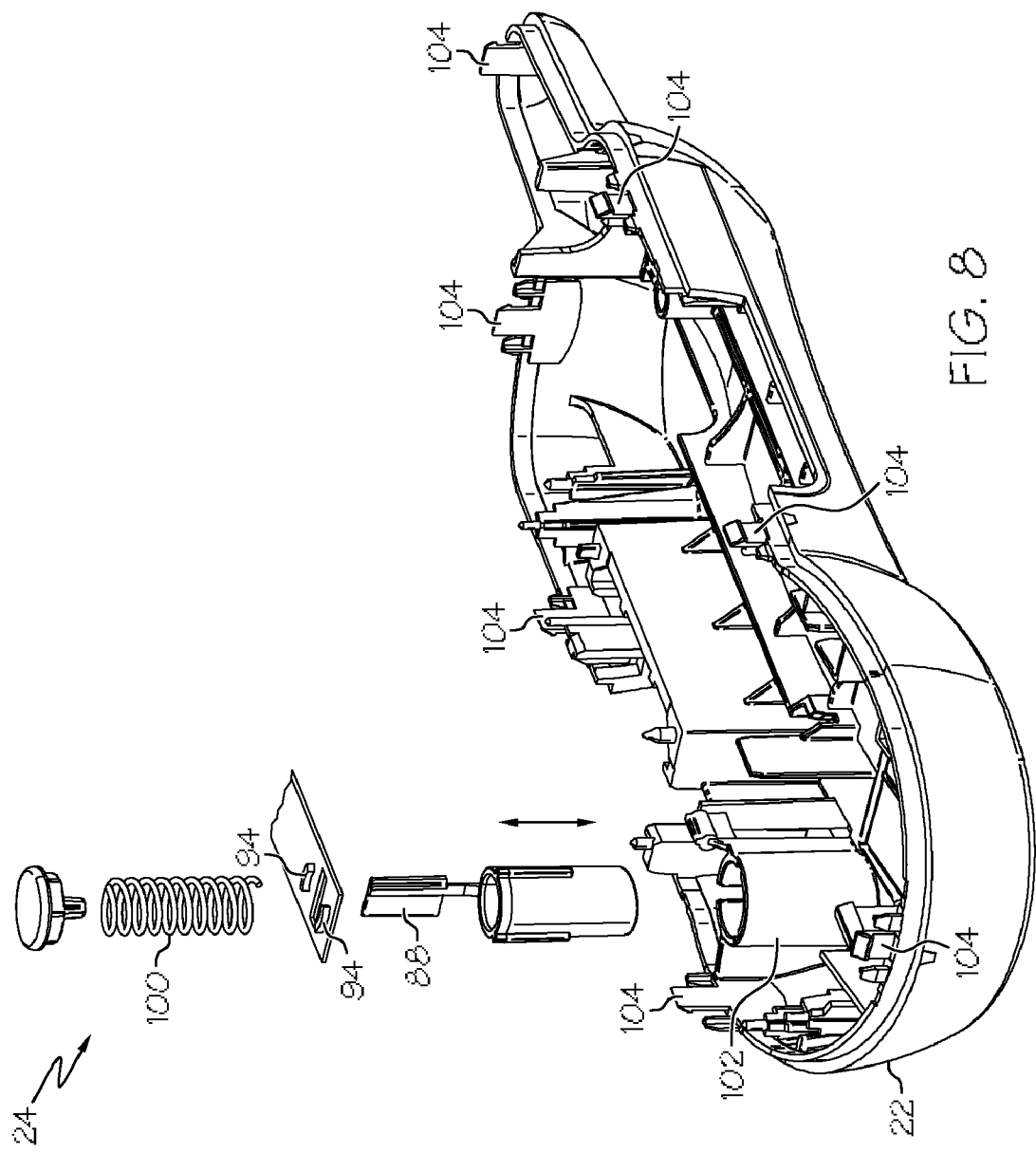

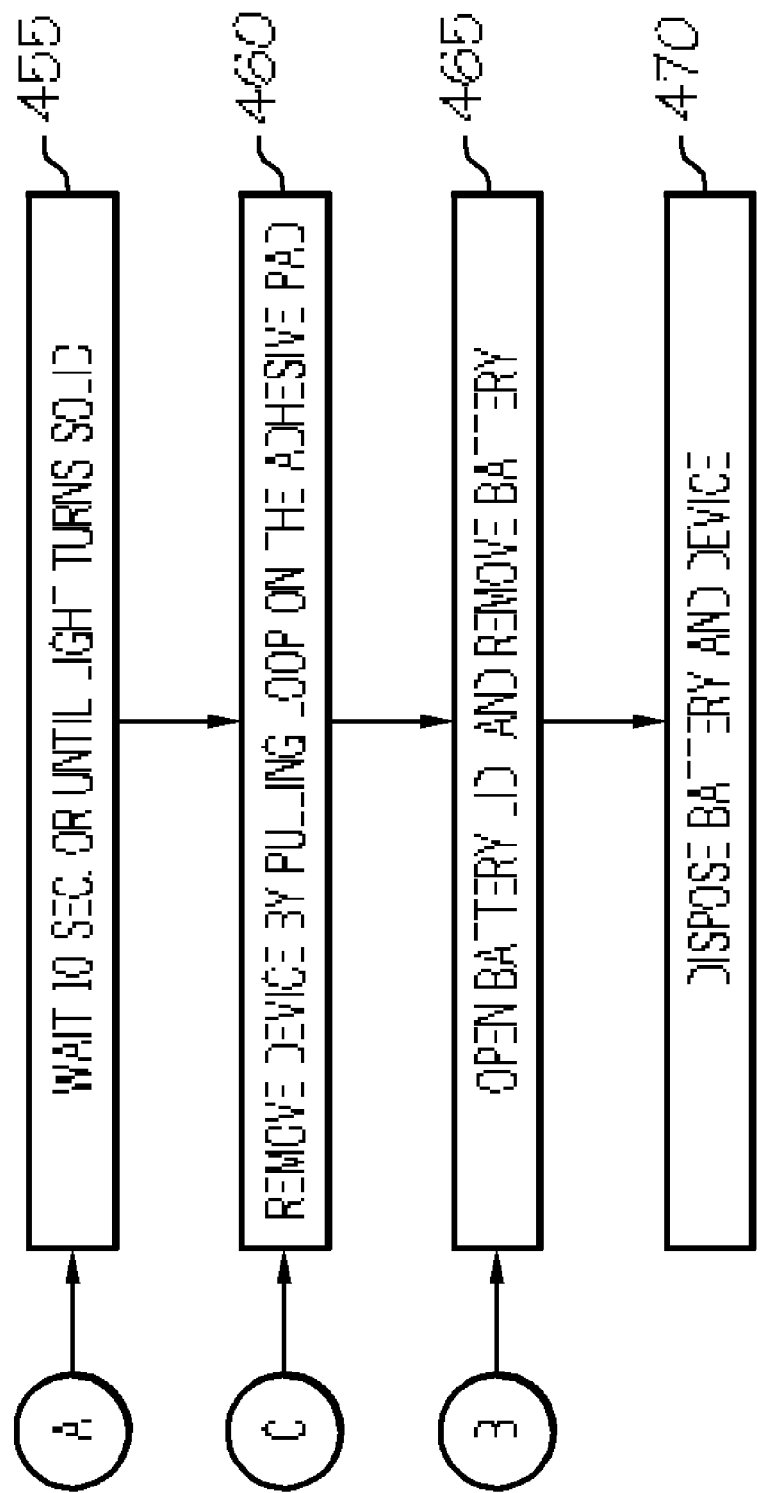

DELIVERY DEVICE FOR USE WITH A THERAPEUTIC DRUG

CROSS REFERENCE TO RELATED APPLICATIONS

This application is a U.S. National Stage Application claiming the priority of co-pending PCT Application No. PCT/EP2009/061592, filed Sep. 8, 2009, which in turn, claims priority to U.S. Provisional Application No. 61/095,667, filed Sep. 10, 2008. Applicants claim the benefit of 35 U.S.C. §120 as to the PCT Application and priority under 35 U.S.C. §119 as to the U.S. Provisional Application, and the entireties of which are hereby incorporated by reference.

TECHNICAL FIELD

The present invention generally relates to a drug delivery device for dispensing medication. More specifically, it relates to a compact and single use, pre-assembled, pre-filled, self-administration device for delivering a therapeutic drug into the body of a user via pumping.

BACKGROUND

Medical devices that deliver medication into the body of an individual via pumping are known and commonly used in the medical industry. Typically, the medication that is delivered from such medical devices depends on the medical condition that is sought to be treated.

For some treatments, such as for example, cancer treatments, it is common for the patients to go to a medical facility to be administered into their body a high volume of a medication. Such a process typically involves a health care provider preparing an infusion set for connection to an external pumping device, inserting a cannula or hollow needle of the infusion set into the patient, and monitoring the progress of the infusion. However, this process is expensive due to the use of a medical facility and the health care provider's time, and can be time consuming in terms of the patient having to travel to and from the medical facility.

Single use, drug delivery devices are known, such as injection pens and disposable infusion devices. However, in the case of injection pens, the use of such pens to administer medication into the patient, which may take more than a few seconds, can be extremely difficult to keep the pen steady especially for a self-medicating patient. Comfort and safety of the patient would thus be an issue when administering higher volumes of medication (e.g., 5 ml or greater). With known disposable infusion device, the patient/user typically has to load a cartridge or in some cases connect an infusion set which makes introducing contaminates into the drug delivery process a potential issue.

Therefore, there is a need in the medical industry to have the flexibility to have the patients pump such liquid drugs in the privacy of their home. Accordingly, there is a further need to develop devices that will administer therapeutic drugs that are easy, convenient and safe to use in the home environment. In addition, there is a need to develop a device that can deliver a range of drugs of different viscosities and volumes to the user/patient.

SUMMARY

It is against the above background that the present invention provides certain unobvious advantages and advancements over the prior art.

According to the invention, a drug delivery device as defined in the independent claim 1 is provided. Further advantageous embodiments of the invention are disclosed in the dependent claims.

Embodiments of the drug delivery device according to the present invention are each a disposable, pre-filled device intended for pumping a drug into the body of a user. As the drug delivery device includes the drug, no final assembly by the user is needed as the device with the drug is ready-for-use out of the box. In addition to the drug being provided in a sterile environment, via a cartridge of the device that helps facilitates long term storage (up to several years, e.g., 5 years), the device is safer to use since the drug requires no handling and hence lessen the chance of introducing contaminates into the drug delivery process.

It is to be appreciated that a final connection between the device and the cartridge containing the drug occurs automatically by the device after activation when use with the user's body. As such, it is not necessary for the user to handle and connect a drug cartridge and/or prime an infusion set before use, thereby increasing which increasing safety and sanitation. Furthermore, as the hollow needle is contained in the device before and after use, such is neither handled nor seen by the user, which further increases safety, sanitation, and is helpful for users having a fear of needles. The device also provides an easy to understand user interface to initiated pumping of the drug as well as multiple visual indicators providing feedback to the user during the entire drug delivery process. Accordingly, a safer and easier to use device is provided. In addition, the device is adaptable for the delivery of different drugs during the manufacturing process. In particular, the device is capable of pumping a variety of drugs and volumes at a substantially constant flow rate. Therefore, the device lowers manufacture cost by having to support only a single platform that can handle a variety of drug delivery needs, such as for example, subcutaneous, intramuscular, or intradermal infusing or injecting of drugs into the body of a user.

In one preferred embodiment, a drug delivery device for pumping medication into the body of a user is disclosed. The device comprises a housing having a start button and a status indicator; and a cartridge holder having a sterile barrier at a first end thereof and arranged in the housing. A cartridge containing a volume of the medication to be dispensed is also provided as well as a drive unit having a plunger. The plunger is movable from a first position adjacent the sterile barrier to a second position in which the plunger has moved through the sterile barrier and the plunger has dispensed the volume of the medication from the cartridge. The device also comprises a transfer unit providing a delivery conduit for the volume of medication from the cartridge to an included hollow needle. The transfer unit is connected to a second end of the cartridge holder and together provides an aseptic environment for the cartridge. The transfer unit is configured to extend the hollow needle beyond the housing and retract the hollow needle back into the housing after the hollow needle has been extended and the medication has been dispensed from the cartridge. The device further comprises an electronic control unit which controls the drive unit, and interfaces with the start button and the status indicator. The electronic control unit is configured such that after the start button has been pressed longer than a requisite amount of time, the electronic control unit provides a ready-to-start status signal via the status indicator, and causes the transfer unit to extend the hollow needle and powers the drive unit such that the plunger moves from the first position to the second position.

These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

The following detailed description of the embodiments of the present invention can be best understood when read in conjunction with the following drawings, where like structure is indicated with like reference numerals and in which:

FIG. 2A is a section view of a start button, status indicator, housing top and a PCB according to an embodiment of the present invention taken along section line 2A-2A in FIG. 2 or 3;

FIG. 3 is a side view of a drug delivery device according to an embodiment of the present invention;

FIG. 8 is an exploded view of a housing bottom for a drug delivery device according to an embodiment of the present invention and showing components of a body sensor according to another embodiment;

FIG. 9 is a depiction of components of a body sensor according to another embodiment of the present invention;

FIGS. 20A and 20B are a flow chart depicting a method of infusing medication utilizing a drug delivery device according to the present invention.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

DETAILED DESCRIPTION

The following description of the preferred embodiments is merely exemplary in nature and is in no way intended to limit the invention or its application or uses.

Drug Delivery Device Architecture

Figure 1:
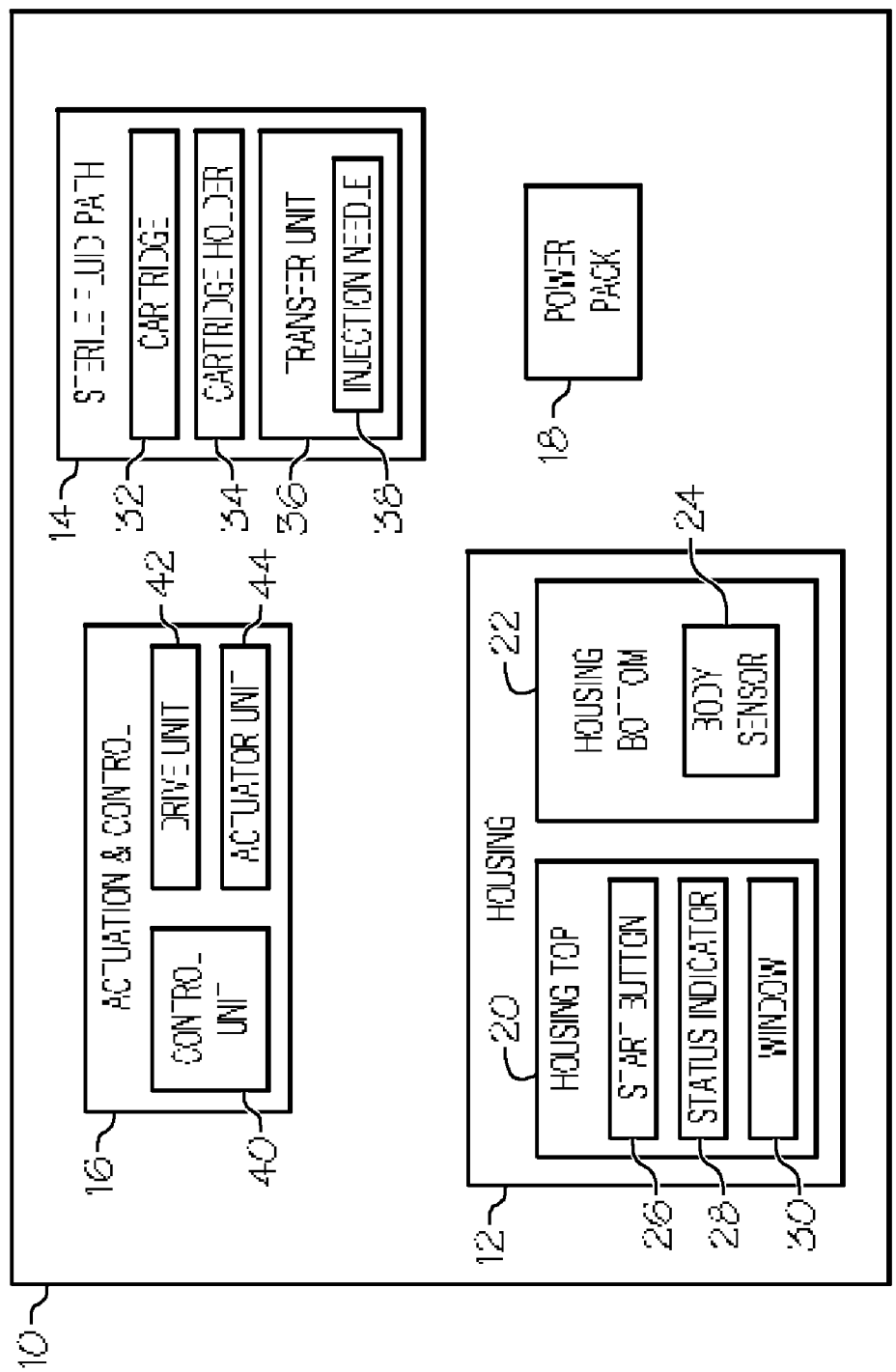
FIG. 1 is a schematic overview of main functional components according to an embodiment of the present invention.

The physical system architecture of a drug delivery device for administering medication into a body of a user is now described hereafter with reference made to FIG. 1. As shown in block diagram, the drug delivery device 10 comprises a housing 12, sterile fluid path components 14, actuation and control components 16, and a power pack 18 for powering the actuation and control components 16. The housing 12 contains all of the device components and provides a means of removably attaching the device 10 to the skin of the user. The housing 12 also provides protection to the interior components of the device 10 against environmental influences. The housing 12 is formed from upper and lower cabinet portions, namely a housing top 20 and a housing bottom 22, and is ergonomically designed in size, shape, and provided features for handling and use by users who may be physically impaired. An optional body sensor 24 may be provided in one embodiment as a safety feature to ensure that the actuation and control components 16, after receiving a start command, will not engage or use the sterile fluid path components 14 unless the device 10 is in contact with the body of the user (patient) that is to be administered the medication via pumping. In such an embodiment, if after the actuation and control components 16 receives a start command and the body sensor 24 does not indicate body contact, either after completion of the start command, e.g., releasing of a start button, or expiration of a period of time in which body contact needs to be indicated by the body sensor 24, e.g., before a start button timeout, the device 10 will turn off to conserve energy. In a preferred embodiment, the body sensor 24 is electromechanically based wherein further details regarding this embodiment is described hereinafter in later sections. In other embodiments, the body sensor 24 can be mechanically based such as, for example, a mechanical lock out that prevents triggering the start command. In still other embodiments, the body sensor 24 can be electrically based such as, for example, a capacitive- or impedance-based sensor which must detect tissue such that the actuation and control components 16, after receiving a start command, will engage the sterile fluid path components 14.

In one embodiment, the device 10 provides activate means that is used by the user to trigger the start command to the actuation and control components 16. In a preferred embodiment, the activate means is a start button 26 that is provided to the housing top 20 and which is contacts a control switch 46 (FIG. 2A) of the actuation and control components 16. In one embodiment, the start button 26 may be a push button, and in other embodiments, may be an on/off switch, a toggle, or solely control switch 46. The housing top 20 also provides a status indicator 28 and a window 30. In other embodiments, the start button 26 as well as the status indicator 28, window 30, and combinations thereof may be provided on the housing bottom 22 such as, for example, on a side visible to the user when the device 10 is placed on the body of the user. Still further details about the housing 12 are provided hereinafter in later sections in reference to other embodiments.

The sterile fluid path components 14 include a cartridge 32, a cartridge holder 34 which provides an aseptic environment for storing the cartridge 32 within the device 10, and a transfer unit 36. As used herein, the term cartridge means a pre-filled container containing a desired volume of the medicinal or drug product. The cartridge 32 containing the volume of the medication (i.e. drug) and with the device 10 forms a combination product. It is to be appreciated that the cartridge 32 can contain a liquid medication, powder medication or a mixture of liquid and powder. Upon proper activation of the device 10, the transfer unit 36 provides a fluid path or delivery conduit between the cartridge 32 and the body of the user. In particular, the transfer unit 36 provides a hollow needle 38 for delivering the medication into the body of the user. It is to be appreciated that depending on the application site of device 10 on the body of the user and/or length of hollow needle 38, subcutaneous, intramuscular or intradermal administration of the medication is possible. Still further details about the sterile fluid path components 14 are provided hereinafter in later sections in reference to other embodiments.

The activation and control components 16 include a drive unit 42, which provides the drive means for administering the drug into the body of the user, and an actuator unit 44 that triggers the transfer unit 36 to extend the hollow needle 38 in order for the device 10 to administer the drug, and then to retract the hollow needle 38 after administering the drug and elapse of a dwell time. In one embodiment, the dwell time is 10 seconds, and in other embodiments the dwell time may be shorter or longer periods so long as the period is suitable to prevent a backflow of the drug from the body after being administered. The activation and control components 16 also include an electronic control unit 40 that controls all device interactions with the user as well as the drive unit 42 and the actuator unit 44. In one preferred embodiment, the control unit 40 interfaces with the body sensor 24, the start button 26 via control switch 46, and the status indicator 28. The control unit 40 is configured such that after the start button 26 has been pressed, the control unit 40 provides a ready-to-start status signal via the status indicator 28 if device start-up checks provide no errors. After providing the ready-to-start status signal, and in an embodiment with the body sensor 24, if the body sensor 24 is in contact with the body of the user and the start button 26 has been pressed longer than a predetermined time, the control unit 40 will power the actuator unit 44 to trigger the transfer unit 36 to make a fluid connection between the cartridge and the hollow needle, and then to extend the hollow needle 38 into the body of the user. After the hollow needle 38 has been extended, the control unit 40 will then power the drive unit 42 to dispense the drug from the cartridge 32, thereby administering the drug into the body of the user via pumping. During the drug delivery process, the control unit 40 is configured to provide a dispensing status signal via the status indicator 28. After the drug has been administered into the body of the user and after expiration of the dwell time, the control unit 40 then powers the actuator unit 44 again to trigger the transfer unit 36 to retract the hollow needle 38 and after retraction, to provide an okay-to-remove status signal via the status indicator 28.

In one embodiment, the device 10 is capable of delivery of a range of drugs with different viscosities and volumes. For example, in a preferred embodiment, the device is capable of delivering drugs having viscosities ranging from about 1 to about 20 centipoises (cPs) at temperatures typically maintained in a home (e.g., 18 to 24° C.). In another preferred embodiment, the device is capable of delivering a drug at a controlled flow rate that is in the range of about 1 to about 3 milliliters per minute (ml/min) with a repeatability of ±20%. In one embodiment, the flow rate (speed) of the drug delivery process is controlled by the control unit 40 controlling the drive means of the drive unit 42 to provide a constant speed. In other embodiments, other flow rates may be provided by varying the geometry of the fluid flow path or delivery conduit from the cartridge 32 through the hollow needle 38, varying the speed at which a component of the drive unit 42 advances into the cartridge 32 to dispense the drug therein through the hollow needle 38 to apply a constant force/pressure to the drug in the cartridge 32, or combinations thereof. In a preferred embodiment, the hollow needle is a 27 gauge needle and in other embodiments, the hollow needle 38 may be any size needle suitable for the type of drug and drug administration (e.g., subcutaneous, intramuscular, intradermal, etc.) intended. Still further details about the actuation and control components 16 are provided hereinafter in later sections in reference to other embodiments.

In one embodiment, the drug delivery process is started by means of displacing (i.e., pressing) the start button 26 of the device 10 for greater than a requisite amount of time. In a further embodiment, the drug delivery process is started by means of displacing the start button 26 of the device 10 for greater than a requisite time if start-up checks provide no errors.

In other embodiments, in which the body sensor 24 is provided, the drug delivery process also will not start if non-contact is indicated by the body sensor 24, such as when the device 10 is not properly attached to the skin of the user's body. In such a situation, the device 10 will provide a no body contact signal (e.g. flash green/yellow) via the status indicator 28, wherein release of the start button 26 will result in the device 10 powering off. Thereafter, the start button 26 will need to be pressed again for greater than the requisite amount of time, such as for example, after proper body contact has been made by the user in order for the drug delivery process to proceed. If immediately upon pressing the start button 26 start-up checks conducted by the control unit 40 provide no errors, a first signal is then displayed by the device 10 via the status indicator 28, such as a ready-to-start status signal, e.g. indicated by a continuous green light. Thereafter, if the start button 26 has been pressed for longer than the requisite amount of time, and in the embodiment with the body sensor 24 body contact is indicated, then a second signal is displayed by the device 10 via the status indicator 28, such as a dispensing status, e.g. indicated by a flashing yellow light, to signify that the drug delivery process is in progress. During the drug deliver process that control unit 40 will automatically complete the fluid connection between the cartridge 32 and the hollow needle 28, extend the hollow needle 28 below the skin of the user/patient, and administer the drug via pumping. Next, after completion of the drug administering and expiration of a dwell period, the control unit 40 will automatically retract the hollow needle 38 (FIG. 1) and display a third signal via the status indicator 28, such as an okay-to-remove status signal, e.g. indicated by another continuous green light, to signify that the device 10 can be removed as the drug delivery process is completed. In the embodiment with the body sensor 24, as soon as the body sensor 24 indicates noncontact with the body, a fourth signal is displayed by the device 10 via the status indicator 28, such as a remove battery status signal, e.g., indicated by a flashing green light, to signify that the battery is still in the device and should be removed.

Illustrative Embodiments

Figure 2:
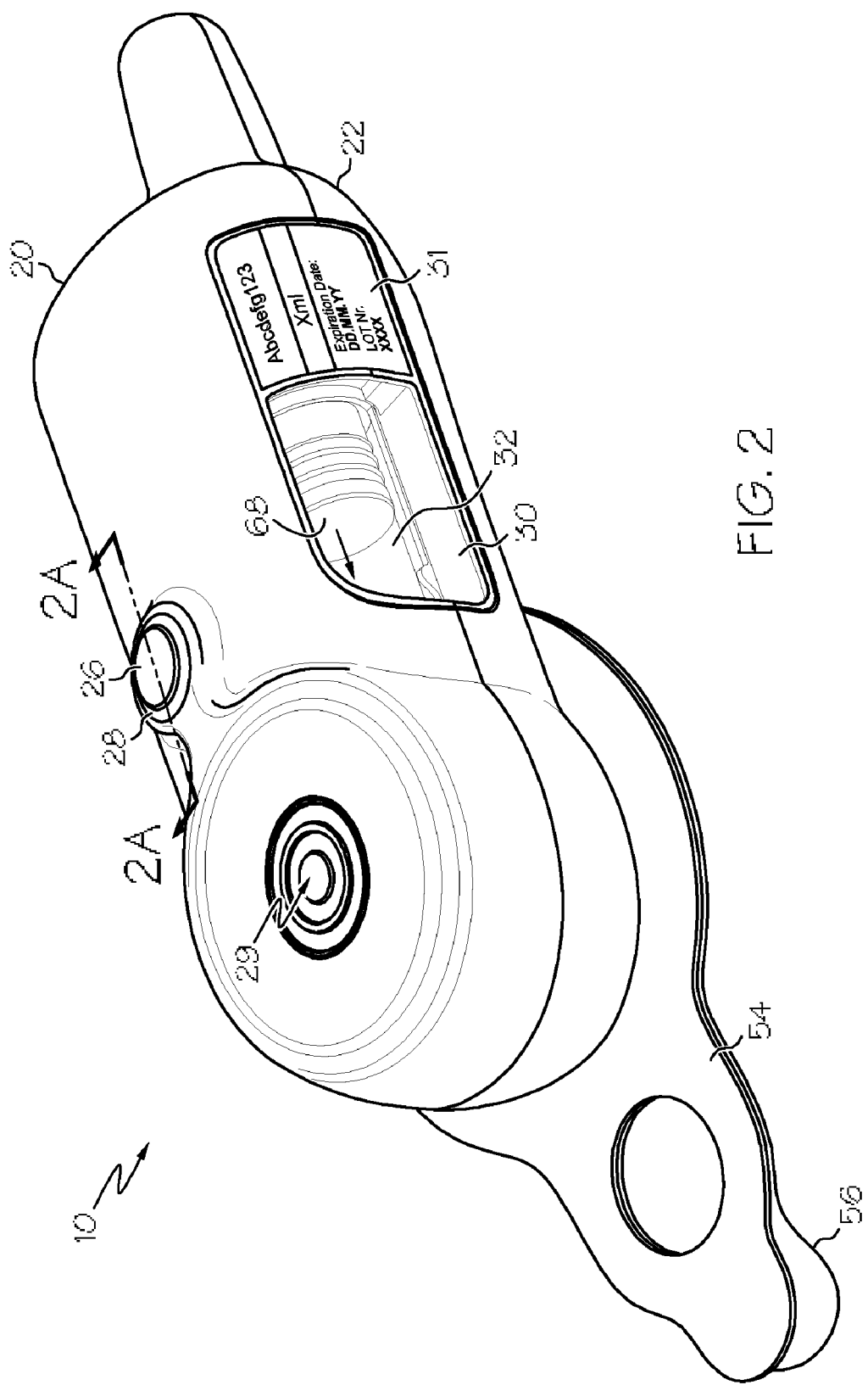
FIG. 2 is a top perspective view of a drug delivery device according to an embodiment of the present invention.
Figure 5:
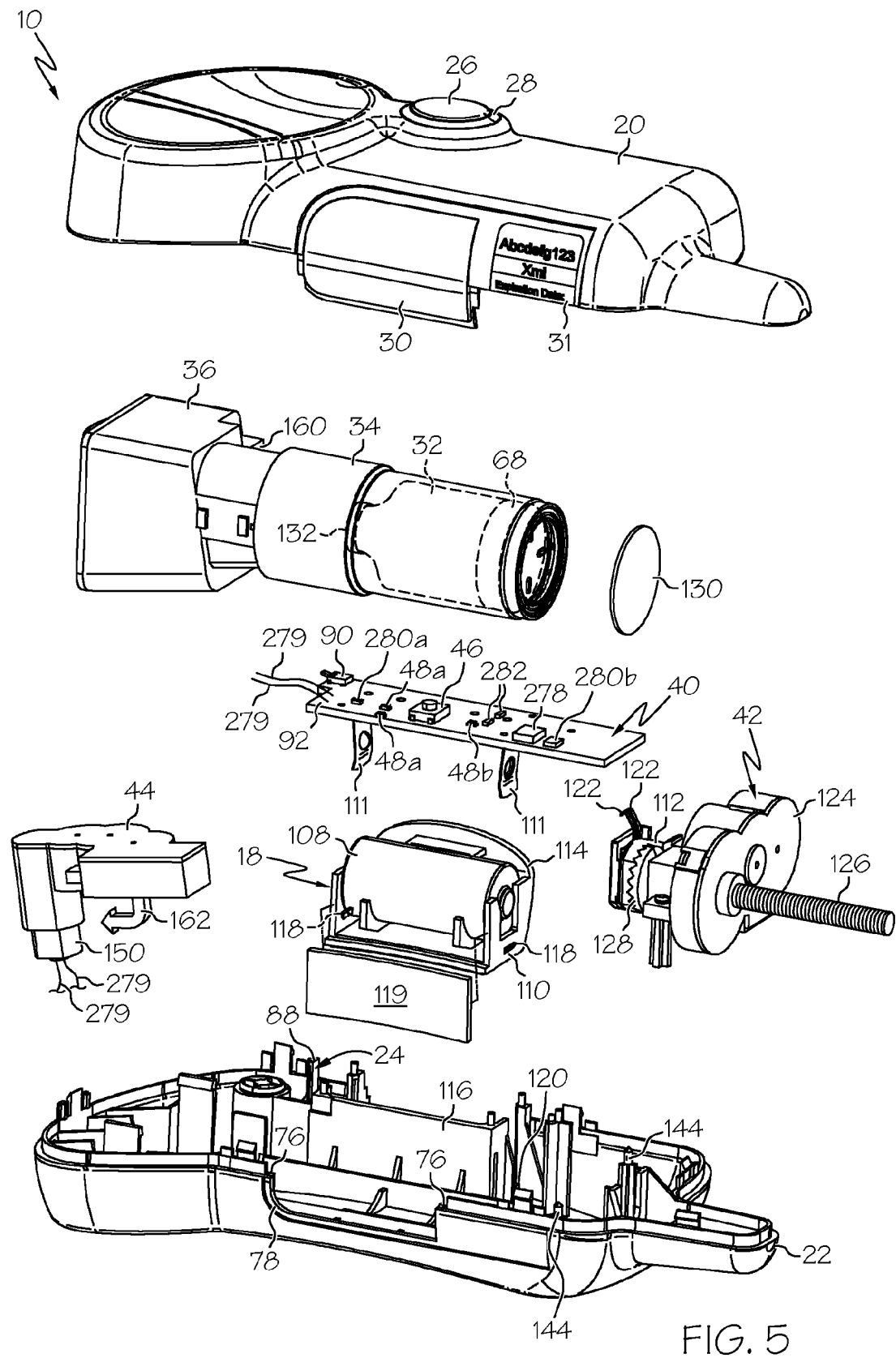
FIG. 5 is an exploded view of a drug delivery device according to an embodiment of the present invention.

Reference now is made to FIG. 2, which depicts a top perspective view of a drug delivery device 10 according to a preferred embodiment. As shown, the housing top 20 provides the start button 26 and the status indicator 28. A marking 29 is also shown in the illustrated embodiment which provides an indication to the user of the location of where the hollow needle 38 will penetrate the skin. The status indicator 28 in the illustrated embodiment is a light pipe that is formed as a translucent ring around the start button 26. It is to be appreciated that the translucent ring of the status indicator 28 situated around the start button 26 enables a provided status indication to be visible when the device 10 is viewed from not only along the longitudinal side (side shown by FIG. 3) but also from above or from any side 360° around the start button 26 due to the status indicator's light pipe design. As shown by FIG. 2A, which depicts a cross-section side view of the device 10 taken along section line 2A-2A in FIG. 2 or 3, the status indicator 28 as well as the start button 26 is raised from the housing top 20 such that the status indicator 28 may be view easily from a side such as shown by FIG. 3. As depicted in FIG. 2A, the start button 26 when pressed contacts the control switch 46 of the control unit 40 that activates the electronics of the control unit 40 which is discussed in greater details in later sections. In this preferred embodiment, the status indicator 28 being a light pipe in the form of a ring, interfaces with at least one light emitting diode (LED), but preferable a pair of LEDs, with a first LED 48a providing a first color and a second LED 48b providing a second color in order to provide two visually different signals. For example, one of the LEDs may be a green LED, and the other may be a yellow LED. Other colors are equally useable. In another embodiment, an additional one of the first LED 48a may be provided as shown in FIG. 5 such that a visibly brighter signal of the first color can be viewed by the user to better interpret a signal, and/or the pair of LEDs 48a, 48b may be arranged in a way that each of their position also helps the user to interpret a provided signal such as, for example, the LEDs 48a, 48b being provided on opposite sides of the start button 26 as shown by FIGS. 2A and 5. In other embodiments, the status indicator 28 may just be at least one LED 48 provided to the housing top 20 (or housing bottom 22) in a location that is visible to the user, such as for example on the side shown by FIG. 3. In still other embodiments, other forms of solid-state lighting (SSL), such as for example, organic light-emitting diodes (OLED), polymer light-emitting diodes (PLED), or laser diodes as well as other sources of illumination such as those based on electrical filaments, plasma, or gas may be used for the status indicator 28. In yet another embodiment the status indicator 28 may be a mechanically based indicator such as to provide a pop up flag(s) or a wheel which turns to display one of two visually different signals (e.g., in color and/or pattern).

In the illustrated embodiment shown by FIG. 3, the housing bottom 22 provides a curvature or contoured (concave) surface 50 to its exterior surface. In other embodiments, the house bottom 22 may be a generally flat surface. The contoured surface 50 in the illustrated embodiment provides a means in which to ensure that an adhesive layer 54 (e.g., an adhesive bandage, sticking plaster) provided by the housing bottom 22 follows the contours of the user's body and firmly attaches to the user's skin in the area of application during the drug delivery process. The adhesive layer 54 may provide any suitable skin friendly adhesive, such as, for example a silicone gel adhesive which has the bonding strength to hold the weight of the device 10 when attached to the user's skin in the application area but which can also be peeled off by the user without damaging the user's skin. The adhesive layer 54 also comprises a flexible carrier material, such as a fabric, a paper, latex or a polymer. In one preferred embodiment, the adhesive layer 54 comprises a woven carrier material that provides a first adhesive on a first surface, which is used to contact the user, and a second adhesive on the opposite surface, which is used to bound the carrier material to the housing bottom 22. In other embodiments, the adhesive layer 54 may comprise a carrier material provided with only the first adhesive on the first surface and bonded to bottom housing by another attachment method such as for example, thermal welding, ultrasonic welding, etc., if the carrier material is provided as a polymer. The adhesive layer 54 may also provided a plurality of aeration perforations for the wear comfort of the user. In another embodiment provided with the body sensor 24, the contoured surface 50 may be such that the body sensor 24 cannot contacted or unintentionally operated when the device 10 is supported by a horizontal surface such as, for example, a table or counter top, that is indicated by dotted line 52.

Figure 4:
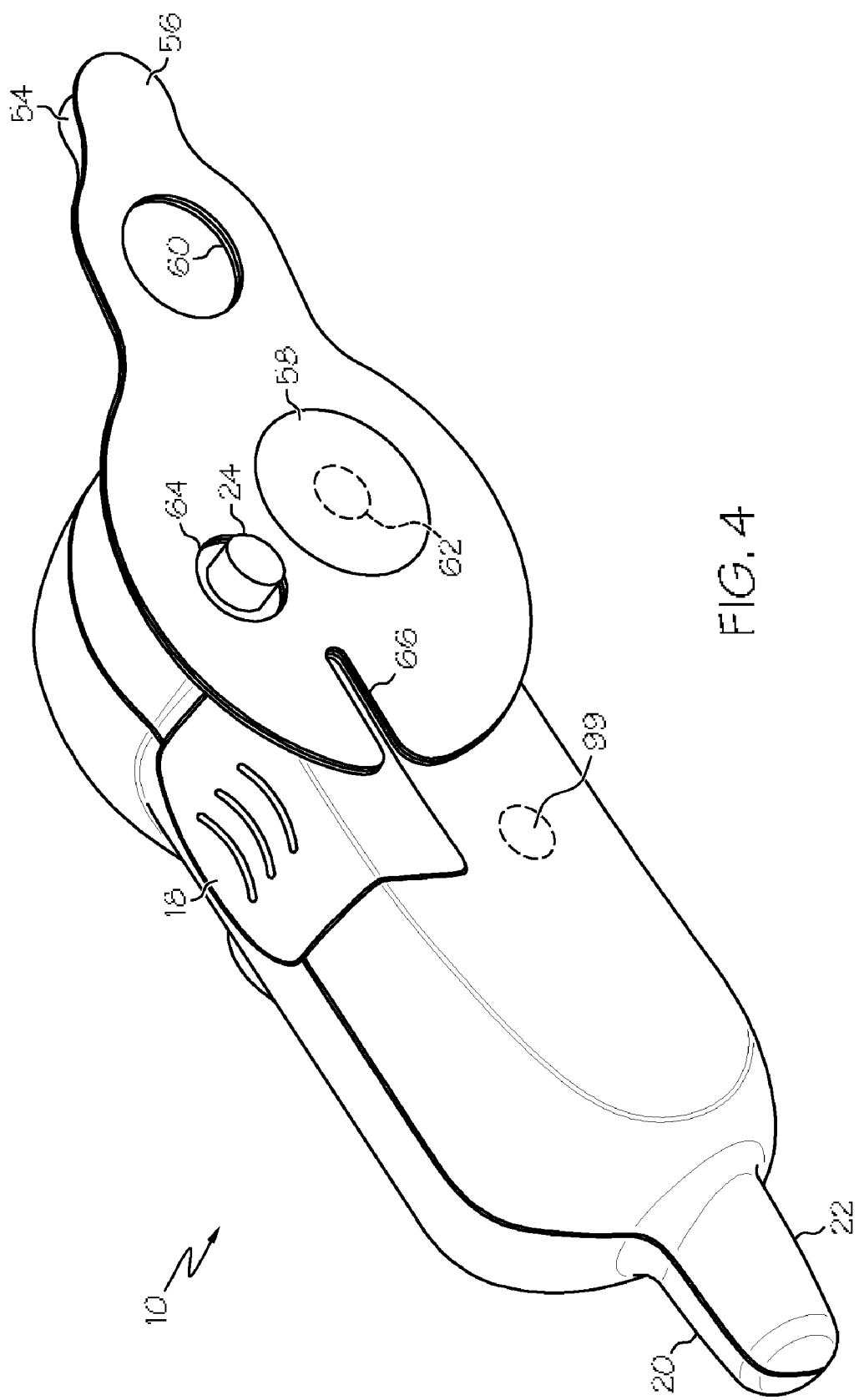
FIG. 4 is a bottom perspective view of a drug delivery device according to an embodiment of the present invention.

As best shown by FIG. 4, which shows a bottom view of the device 10, the adhesive layer 54 is protected in a non-use condition by a removable release liner 56. The release liner 56 protects the adhesive layer 54 until the user is ready to attach the device 10 to his or her body. The release liner 56 may be any suitable release material that may be applied removably to the release liner 56 such as a paper or plastic based carrier material (e.g., super-calendared kraft paper, glassine, clay coated paper, glazed paper, BO-PET film, BOPP film, polyolefins) which is coated on one or two sides with a release agent, such as silicone or other materials that have a low surface energy and which provides a release effect against the adhesive layer 54. The release liner 56 when removed from the adhesive layer 54 also removes a sterile patch 58 which both protects and indicates the location of a port through which the hollow needle 38 (FIG. 1) will extend and retract. It is to be appreciated that the port is provided with a sterile barrier 62 that is bonded to the adhesive patch 58 such that removal of the release liner 56 will also remove both the adhesive patch 58 and the sterile barrier 62 attached thereto. Such an arrangement minimizes the potential for particles from the sterile barrier to be transferred unto the hollow needle 38 when extended automatically from the device 10. As also shown by FIG. 4, the body sensor 24 when provided is unaffected by the adhesive layer 54 and release liner 56 as it is provided with an aperture 64 through which to move unhindered.

To help facilitate easier removal of the device 10 from the body of the user, a ring portion 60 is provided to the adhesive layer 54 which may be gripped by a finger of the user. Additionally, in the illustrated embodiment, a slit 66 is provided in the adhesive layer 54 (and the release liner 56) such that the power pack 18 may be attached to a portion of the adhesive layer 54. Such an embodiment may be provided for the convenience of the user such that when the power pack 18 is removed from the device 10, the power pack does not fall away from the device unintentionally. After removing the power pack 18 from its engagement with the housing top and bottom 20, 22, the user can then separate the power pack 18 from the adhesive layer 54 by simply pulling on the power pack 18. In still other embodiments, the power pack 18 need not be attached to the second surface of the adhesive layer 54, and thus may be freely removed from contact with the device 10 after separation from its engagement with the housing top and bottom 20, 22.

Reference is now made to FIG. 5 in which the drug deliver device of FIG. 2 is shown in exploded view. As shown, the drug deliver device 10 includes the power pack 18, the housing top and bottom 20, 22, the cartridge holder 34 connected to transfer unit 36, the control unit 40, the drive unit 42, and the actuator unit 44. Each one of these components is discussed hereinafter in greater detail.

Housing Top

The housing top 20 represents the top shell or portion of the housing 12 (FIG. 1) and as mentioned previously above provides the start button 26, the status indicator 28, and the window 30. In a preferred embodiment, the window 30 is provided on a side formed between the housing top and bottom 20, 22. In such a side location, the window 30 enables inspection of the content of the drug cartridge 32 and movement of a stopper 68 therein during the drug delivery process, with both being visible through the cartridge holder 34. It is to be appreciated that having the movement of the stopper 68 viewable in the window 30 during the drug delivery process provides another form of continuous optical feedback in addition to the dispensing status signal provided via the status indicator 28 to the user. In still another embodiment, the window 30 can provide a magnifying effect and/or be recessed in the side of the housing 12 to be closer to the cartridge holder 34. In other embodiments, the window 30 may just be an opening that is provided in the housing 12 instead of a separate transparent or crystal clear material as provided in the illustrated embodiment. In still other embodiments, the window 30 may be defined by portions (or all) of the housing top 20 and/or the housing bottom 22 being transparent or crystal clear. In still other embodiments, an additional feature may be provided to the cartridge holder 34 to increase visibility of the contents and stopper 68 of the cartridge 32 such as, for example, providing a reflective or color coating, like white, to the side of the cartridge holder 34 that is directly opposite to the side closest to the window 30. In still another embodiment, the contents of the cartridge 32 could be illuminated such as with a LED, if desired.

Accordingly, in a preferred embodiment, the following user interfaces are provided by housing top 22: the start button 26, the status indicator 28, and the cartridge window 30. Each of the user interfaces has the following functions: the start button 26 start the drug delivery process; the status indicator 28 provides a continuous signal, such as a green continuous signal, to indicate the operating state of the device e.g. ready to start, and a flashing signal, such as a flashing yellow signal, to indicate the operating state of the device e.g. drug injection active, and/or an alternating flashing green/yellow signal to signal a warning, e.g., no body contact; and the cartridge window 30 enables the inspection of the content of drug cartridge 32. Labeling 31 providing information, e.g., drug expiration date, lot number, use instructions, etc., may be provided on the device 10 as still another user interface.

Figure 6:
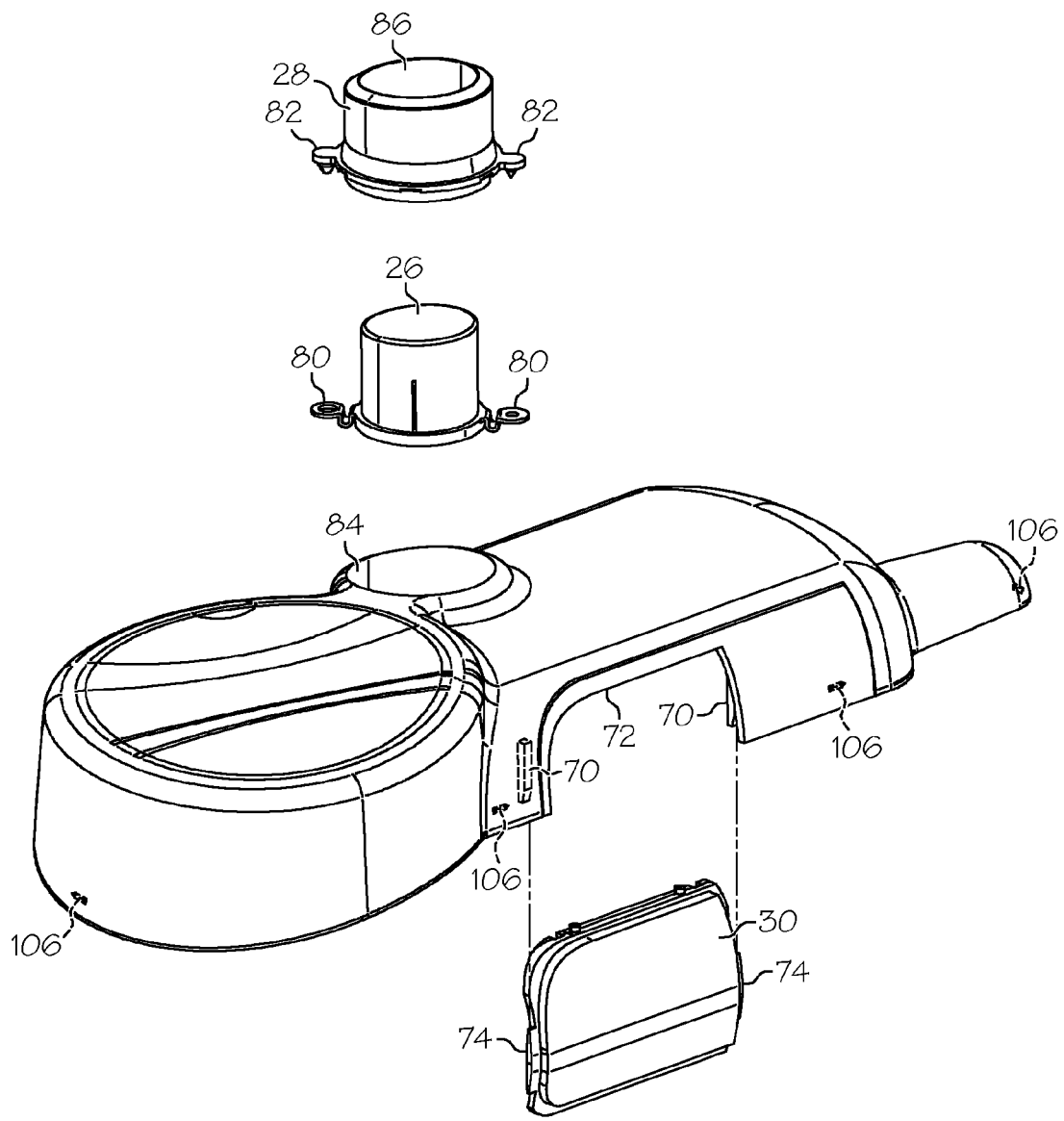
FIG. 6 is an exploded view of a housing top for a drug delivery device according to an embodiment of the present invention.

As shown by FIG. 6, depicting an exploded view of the housing top 20 according to a preferred embodiment, the window 30 is a transparent/crystal clear material, such as a clear plastic, preferably, or glass, that is fitted in a pair slots 70 provided along an upper side cutout 72 of the housing top 20 and mounted therein via thermal bonding or an adhesive. A pair of tongues 74 of the window 30 can be provided which each fit into a respective groove 76 (FIG. 5) provided along a lower side cutout 78 of the housing bottom 22 when the housing top and portions are connected together to form the housing 12. The start button 26 in one embodiment is a polymer that can be displaced via a degree of elasticity such that it may be pressed downwardly into the housing top 20 and which will return automatically to its non-use state after being pressed. In the illustrated embodiment, the degree of elasticity is provided by a pair of flexible tabs 80 that are mounted to an interior side of the housing top 20. The flexible tabs 80 in one embodiment is thermal welded to the interior side of the housing top 20 along with rigid tabs 82 of the status indictor 28. In other embodiments, both tabs 80, 82 can be mechanically attached via threaded screws or via an adhesive. In the illustrated embodiment, the start button 26 as well as the status indicator 28 extends upwardly through a cavity 84 of the housing top 20. However, unlike the start button 26, the status indicator 28 in the preferred embodiment is a relatively, non-flexible translucent polymer which will remain fixed in the cavity 84 via the mounting of the rigid tabs 82 to the housing top 20. In this manner, the status indicator 28 will remain fixed even as the start button 26 is moved down and up within a cavity 86 of the status indicator 28 when pressed. In still other embodiment, the down and up motion of the start button 26 may be provided by an included spring (not shown) such as provided between the start button 26 and the control switch 46.

Housing Bottom

Figure 7A:
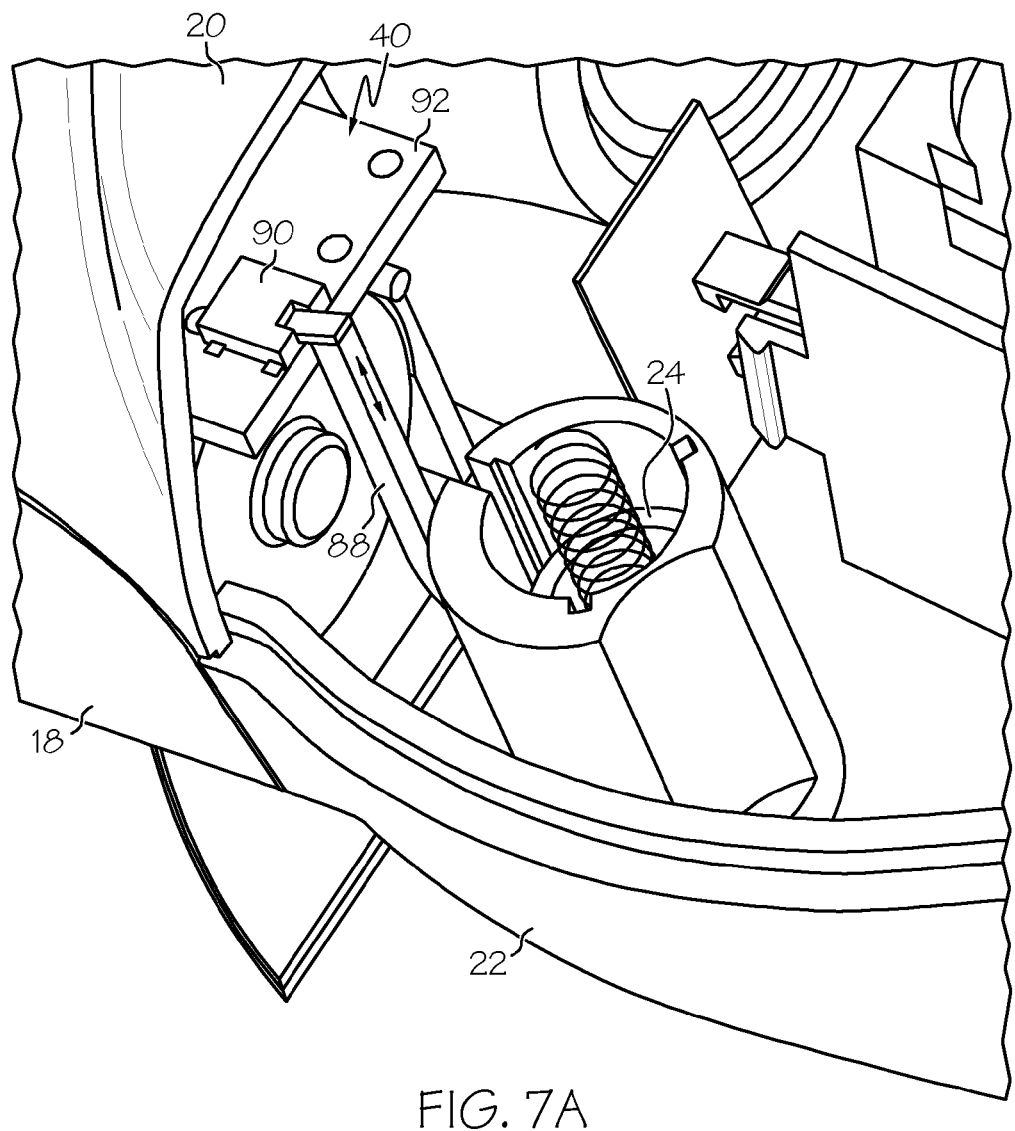
FIG. 7A is close-up, partial section view showing interior components of a body sensor of drug delivery device according to an embodiment of the present invention.
Figure 7B:
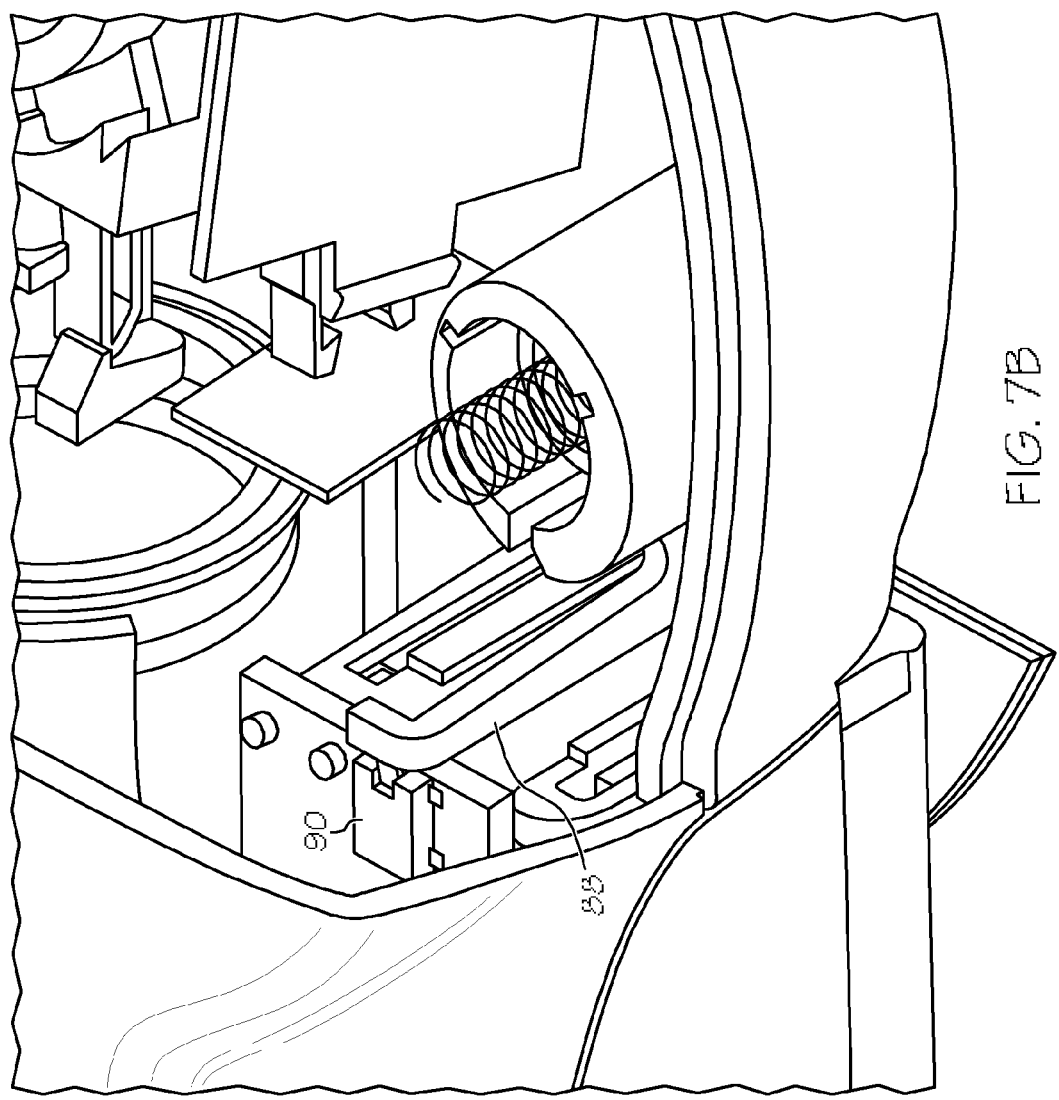
FIG. 7B is close-up, partial section view showing interior components of a body sensor of drug delivery device according to another embodiment of the present invention.

Referring again to FIG. 5, the housing bottom 22 represents the bottom shell or portion of the housing 12. The housing bottom 22 provides mounting locations for all the interior system components and as mentioned above provides the body sensor 24 in one embodiment. In a preferred embodiment, the body sensor 24 is an electromechanical body detection switch and comprises a push rod 88 operatively connected to a switch 90. The push rod 88 is used to detect body contact and signal body contact to the electronic control unit 40 by means of the operating the switch 90 being displaced by the push rod 88 when the device is attached or removed from the body of the user. The switch 90 is best shown by FIG. 7A and in the illustrated embodiment, the switch 90 is a circuit breaker (e.g., single pole, single throw micro-switch) wherein the push rod 88 in a non-displaced state lies below the switch 90. In this illustrated embodiment, the switch 90 is mounted at the edge of a printed circuit board 92 of control unit 40. Accordingly, upward movement of the push rod 88 of the body sensor 24, such as when being displaced by contact with the user's body, will throw the switch 90 to close (complete) a circuit of the control unit 40 to signal body contact to the control unit 40. In an alternative embodiment shown by FIG. 7B, the push rod 88 of the body sensor 24 is mounted above the switch 90. In such a configuration, movement of the push rod 88 of the body sensor 24, such as from being displaced by contact with the user's body, throws the switch 90 to close (complete) a circuit of the control unit 40 to signal body contact to the control unit 40. In still other embodiments, the displacement of the push rod 88 may open a circuit of the electronic control unit 40 to signal body contact. Should at any time during the drug delivery process, the push rod 88 not remain displaced e.g., pressed, such as if the device is removed from the body of the user, the resulting movement of the switch 90 signals to the control unit 40 noncontact with the body. Thereafter, in such a situation, the control unit 40 will provide the no-body contact signal as mentioned previously above and automatically stops the drive unit 42, thereby halting any further dispensing of the drug from cartridge 32.

In still a further alternative embodiment as depicted by FIG. 8, the body sensor 24 is still electromechanically based and can comprise the push rod 88 operatively connected to a LED and phototransistor pair 94 to create a light beam switch. In one embodiment, movement of the push rod 88, such as when the body sensor 24 is pressed, will break a light beam between the LED and phototransistor pair 94 to signal contact with the body of the user to the electronic control unit 40. In another embodiment, such movement of the push rod 88 can permit a light beam to travel between the LED and phototransistor pair 94 to signal contact with the body of the user to the electronic control unit 40. In both alternative embodiments, the opposite movement of the push rod 88 will result in the control unit 40 providing the no body contact signal as mentioned previously above and automatically stops the drive unit 42, thereby halting any further dispensing of the drug from cartridge 32.

In yet another alternative embodiment as depicted by FIG. 9, the body sensor 24 comprises a magnet 96 provided to the push rod 88 and a reed switch 98 provided to the electronic control unit 40. In one embodiment, movement of the push rod 88 opens the read switch 98 via farther proximity to the magnet 96 when the body sensor 24 is displaced to signal device contact with the body of the user to the electronic control unit 40. In another embodiment, movement of the push rod 88 closes the reed switch 98 due to closer presence of the magnet when the body sensor 24 is displaced to signal device contact with the body of the user to the electronic control unit 40. In both alternative embodiments, the opposite movement of the push rod 88 will result in the control unit 40 providing the no body contact signal as mentioned previously above and automatically stops the drive unit 42, thereby halting any further dispensing of the drug from cartridge 32.

In one embodiment, the push rod 88 is biased by a spring force provided by the switch 90. As shown by FIG. 8, the push rod 88 of the body sensor 24 may also be biased via a spring 100 and accommodated in a cavity 102 provided by the housing bottom 24. In such embodiments, the body sensor 24 will be biased to extend out from the housing bottom 24.

In one preferred embodiment, a snap-fit connection is provided via snap tabs 104 of the housing bottom 22 interlocking with a corresponding number of recesses 106 provided on the interior surface of the housing top 20 (FIG. 6). The snap-fit connection provides a physical joining of the housing top and bottom 20 and 22 that permits the housing 12 to be assembled quickly and independently of gluing with chemical adhesives. This freedom from chemical adhesives opens the way for using a wide variety of chemically resistant plastics for the housing top and bottom 20, 22, which are desirable to use in the medical product environment. In still other embodiment, the housing top and bottom 20, 22 may be joined via thermal bonding or fastening e.g. via screws, rivets, nuts, bolts, studs, etc.

Power Pack

Referring again to FIG. 5, the power pack 18 provides enough power to operate the device 10 for a single drug delivery process. As shown, the power pack 18 comprises a battery 108 to supply the power to the device, and a battery tray 110, which supports and retains the battery 108 to prevent the possibility of a short circuit of the battery during storage, transport, use and disposal. It is to be appreciated that the battery tray 110 is also ergonomically designed to enable a physically impaired user to remove the power pack 18 from the device and separately disposed it thereafter. The power pack 18 interfaces with control unit 40 via electrical connections 111. In one embodiment, the battery 108 is a 1400 milliampere-hour (mAh), 3V rated lithium ion battery, such as battery type CR123A, and in other embodiments may be any other battery type and/or batteries that meet the power requirement of the device 10. The battery tray 110 in one embodiment includes a sidewall 114 that has a shape different from an opposite wall and that only fits into a battery compartment 116 of the housing bottom 22 in only one orientation. The sidewall 114 thus prevents the power pack 18 from being inserted into the battery compartment 116 with the wrong polarity. The battery tray 110 once inserted during assembly is locked in place via a snap fit connection between catches 118 of the battery tray 110 and tabs 120 of the battery compartment 116. In another embodiment, it is to be appreciated that when the user removes the power pack 18 from the device 10, the tabs 120 can be designed to break the catches 118 such that that the battery tray 110 can no longer be inserted into the battery compartment 116 unless this safety feature is disable via abuse. The battery tray 110 also include a cover 119 to protect the battery 108 and which prevents removal of the battery 108 from the battery tray 110 after the power pack 18 has been removed from the device 10, thereby providing improved battery safety by preventing its re-use in another electronic device. Still another benefit is that the power pack 18 is easy to dispose since the battery poles are protected against being short circuited.

Drive Unit

Referring back to FIG. 5, the drive unit 42 is electromechanically based, and transforms the electrical energy provided from the electronic control unit 40 via electrical connectors 122 into mechanical rotation via a motor drive assembly 124. The mechanical rotation is transformed to linear movement via the motor drive assembly 124 moving a plunger 126. The plunger 126 is movable linearly, automatically and continuously, by the motor drive assembly 124 from a first position adjacent a sterile barrier 130 to a second position in which the plunger has been moved through the sterile barrier 130 to dispense a desired volume of the drug from the cartridge 32. In the illustrated embodiment, the plunger 126 is provided with a piercing surface 128. In this embodiment, the first position situates the piercing surface 128 adjacent to a sterile barrier 130 in a non-operative condition. The sterile barrier 130 covers an opening at a first end 183 (FIG. 12) of the cartridge holder 34. The second position is that in which the piercing surface 128 has broken through the sterile barrier 130 and driven the stopper 68 within the cartridge 32 adjacent to a septum closure 132, thereby dispensing the drug from the cartridge.

Figure 10:
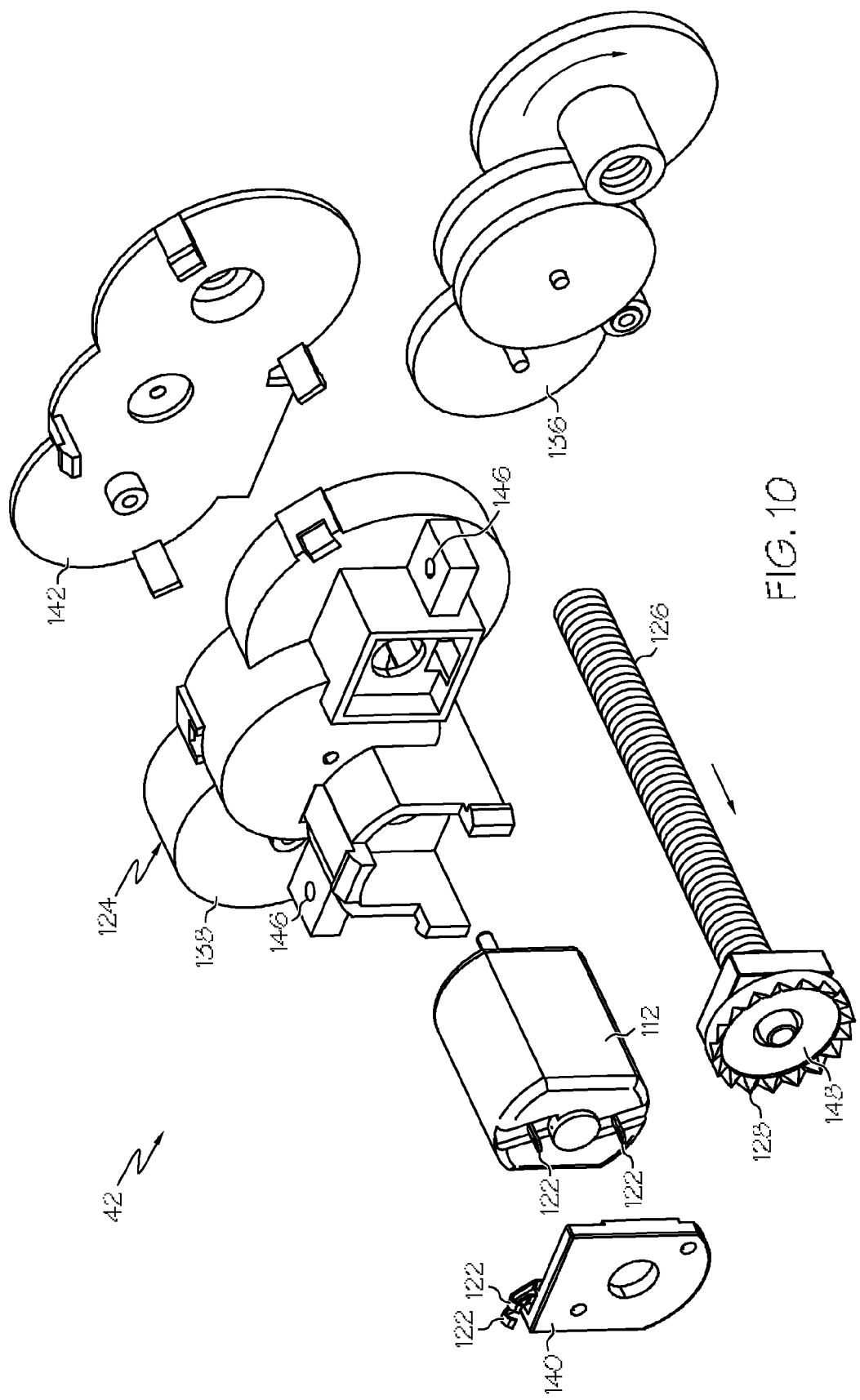
FIG. 10 is an exploded view of a drive unit for a drug delivery device according to an embodiment of the present invention.

As shown by FIG. 10, which depicts an exploded view of the drive unit 42 according to a preferred embodiment, the motor drive assembly 124 includes a motor 134 and a gear set 136 driven by the motor 134. The motor 134 and gear set 136 are arranged in a drive assembly housing 138 with first and second covers 140, 142 snap-fitted thereto. The drive assembly housing 138 is aligned in the housing bottom via pins 144 (FIG. 5) of the housing bottom 22 being situated in corresponding holes 146 provided in the drive assembly housing 138. In one embodiment, the pins 144 are thermally bonded to the holes 146 to fix also the drive unit to the housing bottom. In other embodiments, the drive unit may be fixed to the housing bottom via a mechanical fastener such as a screw.

The gear set 136 when turned by the motor 112 moves the plunger 126. In a preferred embodiment, the plunger 126 is a lead screw that is rotated by a gear of the gear set 136. In another embodiment, the plunger 126 may be provided with teeth that mesh with a gear of the gear set 136 and which is moved linearly without rotation. In the illustrated embodiment, a flange 148 is rotationally coupled to a free end of the plunger 126 and provides the piercing surface 128. It is to be appreciated that the lead screw plunger 126 is free to rotate about the flange 148, especially when the piercing surface 128 of the flange 148 is penetrating through the sterile barrier 130 and when the piercing surface 128 is engaging the stopper 68 without rotation as the plunger 126 rotates and pushes on the flange 148 to move the stopper 68. It is to be appreciated that in still other embodiments, the plunger 126, the piercing surface 128, and/or the flange 148 may be provided integral with each other.

In one embodiment, the motor 112 is a DC motor and rated such that it can operate with an electrical input of 3.0 V at about 1000 mAh or more as limited by the battery 108 for about 1 second at motor start, and at 2.5 V, about 500 mAh continuous. With this motor rating, the motor 112 is able to drive the gear set 136 to drive the plunger 126 at a constant rate of about 7 mm/min under a load of up to approximately 100 to 200 Newton's (N). Additionally, with this motor rating, the plunger 126 is provided with the force to break the sterile barrier 130 of the cartridge holder 34 with the piercing surface 128 of the flange 148 and to move the stopper 68 in the cartridge 32 to administer the drug into the body of the user. In other embodiments, other motor ratings may be provided to match the power and load requirements of the device 10.

Actuator Unit

Figure 11A:
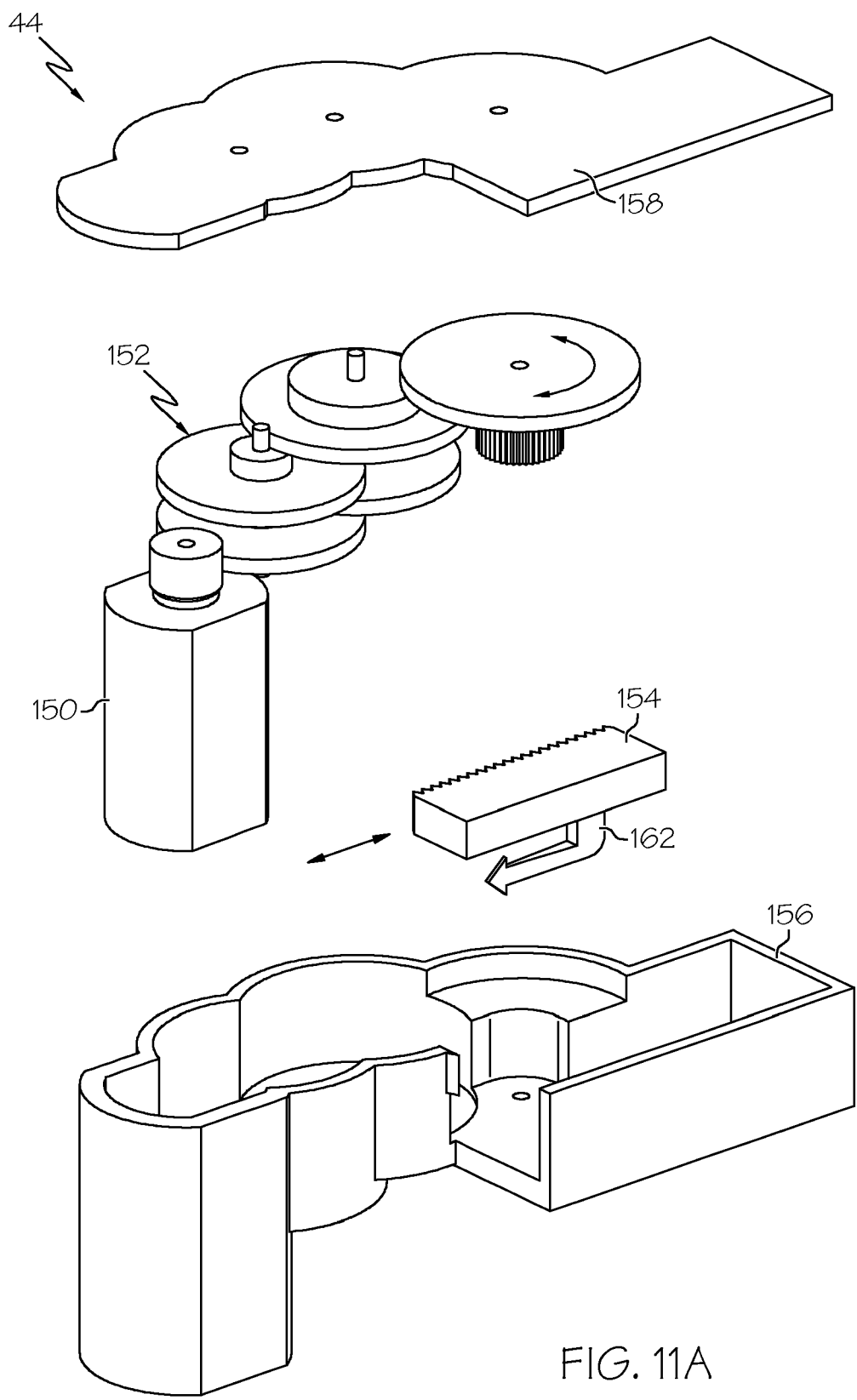
FIG. 11A is an exploded view of an actuator unit for a drug delivery device according to an embodiment of the present invention.

The actuator unit 44 is an electro-mechanical actuator that transforms the electrical energy provided from the electronic control unit 40 into mechanical movement to trigger insertion and retraction of the hollow needle 38 (FIG. 1). With reference to FIG. 11A, which depicts an exploded view of the actuator unit 44 according to a preferred embodiment, the actuator unit 44 includes a motor 150, a gear set 152, and a push rod 154, which area all provided in an actuator housing 156 having a cover 158. The motor 150 turns the gears of the gear set 152 to drive the push rod 154, which triggers the transfer unit to extend and retract the hollow needle 38. The push rod 154 triggers the transfer unit 36 (FIG. 5) to extend the hollow needle 38 (FIG. 1) when driven in a first direction, and to retract the hollow needle 38 when driven in a second direction. In one embodiment, the first direction is that the push rod 154 extends towards the transfer unit 36, and the second direction is that the push rod 154 moves away from the transfer unit 36, in a direction opposite i.e. reverse to the first direction. In still another embodiment, the directions of the push rod 154 movement may be reversed.

It is to be appreciated that the electronic control unit 40 provides power to the motor 150 via an electrical connection (not shown) with a voltage having a first polarity to drive the push rod 154 in the first direction and with a voltage having a second polarity to drive the push rod 154 in the second direction. In one embodiment, the motor 150 is a DC motor and rated such that it can operate with an electrical input of 3.0 V at about 1000 mAh or more as limited by the battery 108 for about 1 second at motor start, and at 2.5 V, about 500 mAh continuous. With this motor rating, the motor 150 is able to drive the gear set 152 to drive the push rod 154 at a constant rate of about 8 mm/min under a load of up to approximately 25 N. Additionally, with this motor rating, the push rod 154 is provided with the force to open and pass through a sterile barrier 160 (FIG. 5) of the transfer unit 36. In one embodiment, the push rod 154 opens and passes through the sterile barrier 160 with a piercing member 162 to trigger the insertion and retraction of the hollow needle 38 (FIG. 1). In other embodiments, other motor ratings may be provided to match the power and load requirements of the device 10. In one embodiment, the minimum travel of the piercing member 162 is at least 8 mm, and in another embodiment may be a lesser distance as long as it meets the triggering requirements of the transfer unit 36.

Figure 11B:
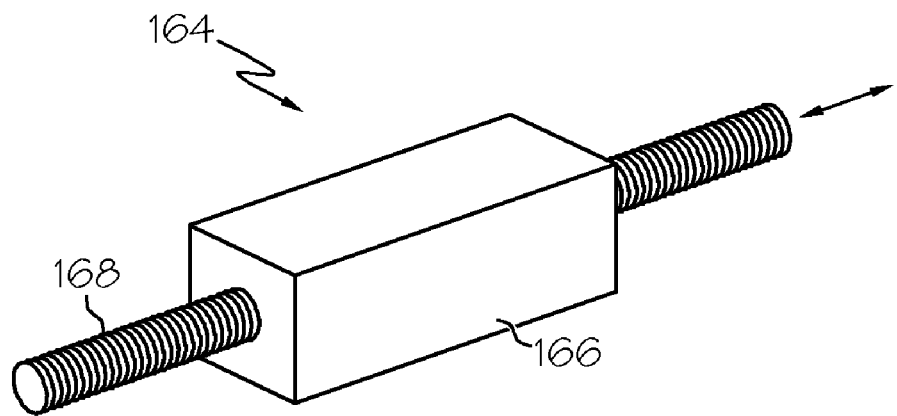
FIGS. 11B and 11C are each an alternative embodiments of an actuator unit for a drug deliver device according to the present invention.

In still another embodiment, a piezoelectric-based actuator 164 may provide the movement of the push rod 154 in both directions. The piezoelectric-based actuator 164 when powered by the control unit 40, via a 2-wire connection, vibrates a nut 166 to cause rotation of a mating screw 168 as shown by FIG. 11B. This rotation of the mating screw 168 then pushes or pulls at least the piercing member 162 to trigger the extension and retraction of the hollow needle by the transfer unit 36.

Figure 11C:
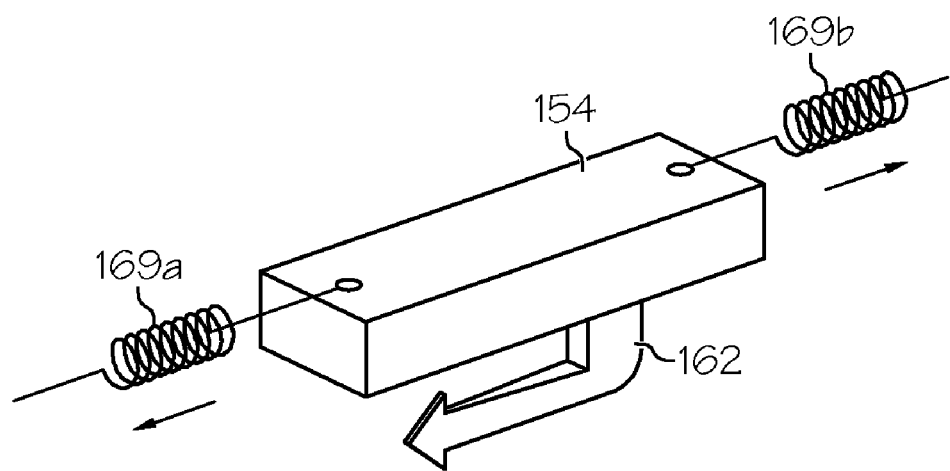

In another embodiment, a shape memory alloy (SMA) actuator 169a may be provided as shown by FIG. 11C. In such an embodiment, the insertion and then the retraction of the hollow needle 38 is provided by two independent strokes of the SMA actuator 169a. That means that the insertion of the hollow needle 38 is triggered by a movement of the push rod 154 in a first direction (first stroke), and the retraction of the hollow needle 38 is triggered by another movement in the first direction (second stroke). Alternatively, a second SMA actuator 169b can be provided in which the first SMA actuator 169a drives the push rod 154 in the first direction and the second SMA actuator 169b drives the push rod in the second direction. In still another embodiment, the second SMA actuator 169b may be replaced by a spring that work together complementary with the first SMA actuator 169a.

Cartridge/Cartridge Holder

Figure 12:
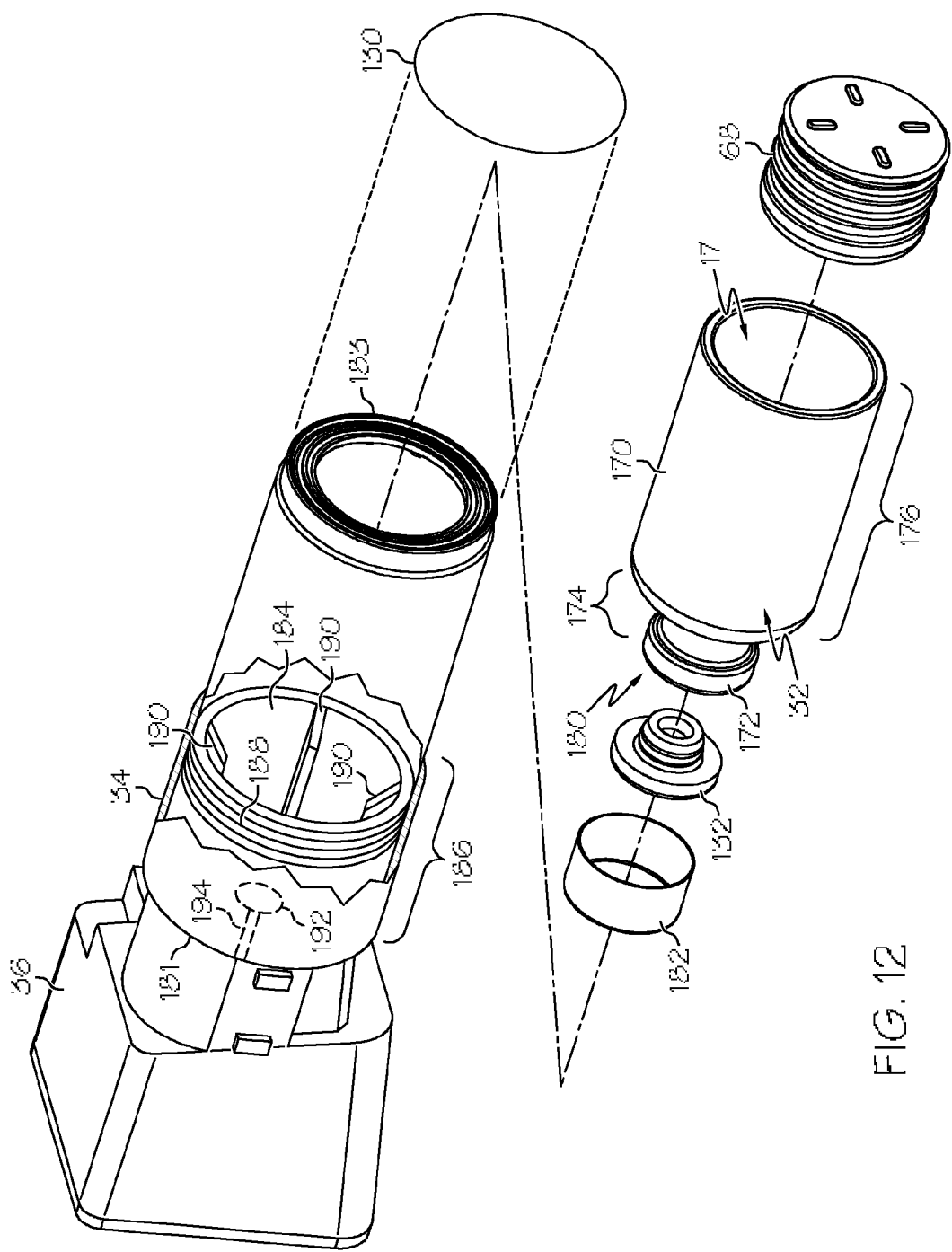
FIG. 12 is a partial exploded view of a cartridge with a cartridge holder partially cut-away and attached to a transfer unit according to an embodiment of the present invention.

Reference to FIG. 12 is now made, which depicts an exploded view of the cartridge 32 provided with the cartridge holder 34 connected to the transfer unit 36. The cartridge 32 is a pre-filled primary container containing the medicinal product. It is to be appreciated that any container that permits dispensing a liquid drug therein from one end via the plunger 126 moving another end may conveniently be used with the device 10 according to the present invention. For example, in the illustrated embodiment of FIG. 12, the cartridge 32 includes a cartridge tube 170 having head, neck, and body portions 172, 174, 176 and a first opening 178 provided at an end remote from the head and neck portions 172, 174. The septum closure 132 is provide to close a second opening 180 of the tube 170 defined by the head portion 172. A ringed band 182 wraps the head portion 172 to seal firmly the septum closure 132 to the head portion 172.

The stopper 68 is provided a distance from the septum closure 132 inside the body portion 176 to define a desired fill volume with the tube 170. In one embodiment, the device 10 with the cartridge 32 is capable of having delivery volumes in the range of 1-15 ml and in other embodiments, greater and/or lesser volumes are possible. In one preferred embodiment, the range of delivery volumes is provided by varying the distance (start positions) of the stopper 68 within the body portion 176 from the septum closure 132. In one preferred embodiment, the range of delivery volumes is provided by pre-filled cartridges 32 provided in different lengths and with varying start positions of the stopper 68.

In one embodiment, in which an inside diameter of the body portion 176 of the cartridge tube 170 is about 19 mm, the different total cartridge lengths (which includes the septum closure) is about 47 mm for dispensing fill volumes of 1-5 ml, about 65 mm for dispensing fill volumes of 5-10 ml, and about 83 mm for dispensing fill volumes of 10-15 ml, with the various volumes being based on the starting position of the stopper 68. In other embodiments, the cartridge may have a dispensing fill volume in the range of 1 to 20 ml based on the starting position of the stopper 68 with an inside diameter in the range of 10 to 30 mm, and a total cartridge length in the range of 20 to 100 mm. In the illustrated embodiment, the stopper 68 may have a generally curved surface. In other embodiments, the stopper 68 may have a flat surface or a surface that corresponds (is complimentary) to the inside shape of the neck portion 174 up to the inside surface of the septum closure 132. As mentioned previously above, movement of the stopper 68 is viewable through the cartridge 32 and cartridge holder 34.

As shown by the cut-away section of the cartridge holder 34, the transfer unit 36 provides a docking port 184 onto which a second end 181 of cartridge holder is fitted over up to a first end portion 186. An O-ring 188 is provided on the docking port 184 to ensure a snug fit with the cartridge holder 34 as well as to help maintain an aseptic environment for the enclosed cartridge 32 that is formed between the transfer unit 36 and the cartridge holder 34 after sterilization. In another embodiment, the cartridge holder 34 may be connected to the docking port 184 via a threaded screw engagement, laser welding, ultrasonic welding, adhesive bonding or combination thereof so long as the aseptic environment can be maintained during the shelve life of the device 10. The docking port 184 in the illustrated embodiment provides supports 190 that are sized and shaped to support axially at least the head portion 172 of cartridge 32 about the ringed band 182 when the cartridge is provided in the cartridge holder 34 and the cartridge holder 34 is attached to the transfer unit 36. These supports 190 ensure that the axial load force generated by the plunger 126 (FIG. 5) is not carried by the head portion 172, but rather transferred to the supports 190 during movement of the stopper 68. In another embodiment, these supports 190 may be provided by the interior surface of the cartridge holder 34 or by a separate support which fits around the neck portion 174.

As shown, another sterile barrier 192 is provided inside the docking port 184 to cover a centrally located port through which a cartridge needle 194 extends to pierce the septum closure 132 in order to complete the fluid path or delivery conduit for the medication provided inside the cartridge 32 to the hollow needle 38 during the drug delivery process. The sterile barrier 192 further helps to provide the aseptic environment formed between the cartridge holder 34 and the transfer unit 36 once sterilized. It is to be appreciated that the sterile barriers 58, 62, 130, 160, 192 are each a sterile barrier material that ensures that no foreign particles, such as dust, or airborne microorganisms can enter into the cartridge holder 34 and transfer unit 36 once combined. Suitable sterile barrier materials include metal or alloys foils, papers, non-woven and plastic materials, which can be attached via thermal welding, ultrasonic welding, adhesive bonding or combination thereof to help provide and maintain the aseptic environment for the cartridge 32 provided by the cartridge holder 34 and transfer unit 36 in their initial non-use state during the shelve life of the device 10. It is further to be appreciated that the septum closure 132 is also of a material, such as for example, silicone, PVDC lined silicon, PTFE lined silicone, and the likes, that ensures that no particles enter or are released into the medication due to material breakage when pierced by the cartridge needle 194. Greater details regarding the cartridge needle 194 is provided hereinafter in a later section.

The cartridge 32 is either clear glass preferable or a transparent medical plastic that is non-reactive to the medication, and which is compatible with steam-, heat-, gamma-, electron beam- or gas (ethylene oxide)-sterilization. The cartridge holder 34 is either clear glass preferable or a transparent medical plastic which is compatible with gamma-, electron beam- or gas (ethylene oxide)-sterilization. Examples of some suitable medical plastics, and not limited there to, include polyethylene terephthalate (PET), and glycol-modified polyethylene terephthalate (PETG).

Transfer Unit

Figure 13:
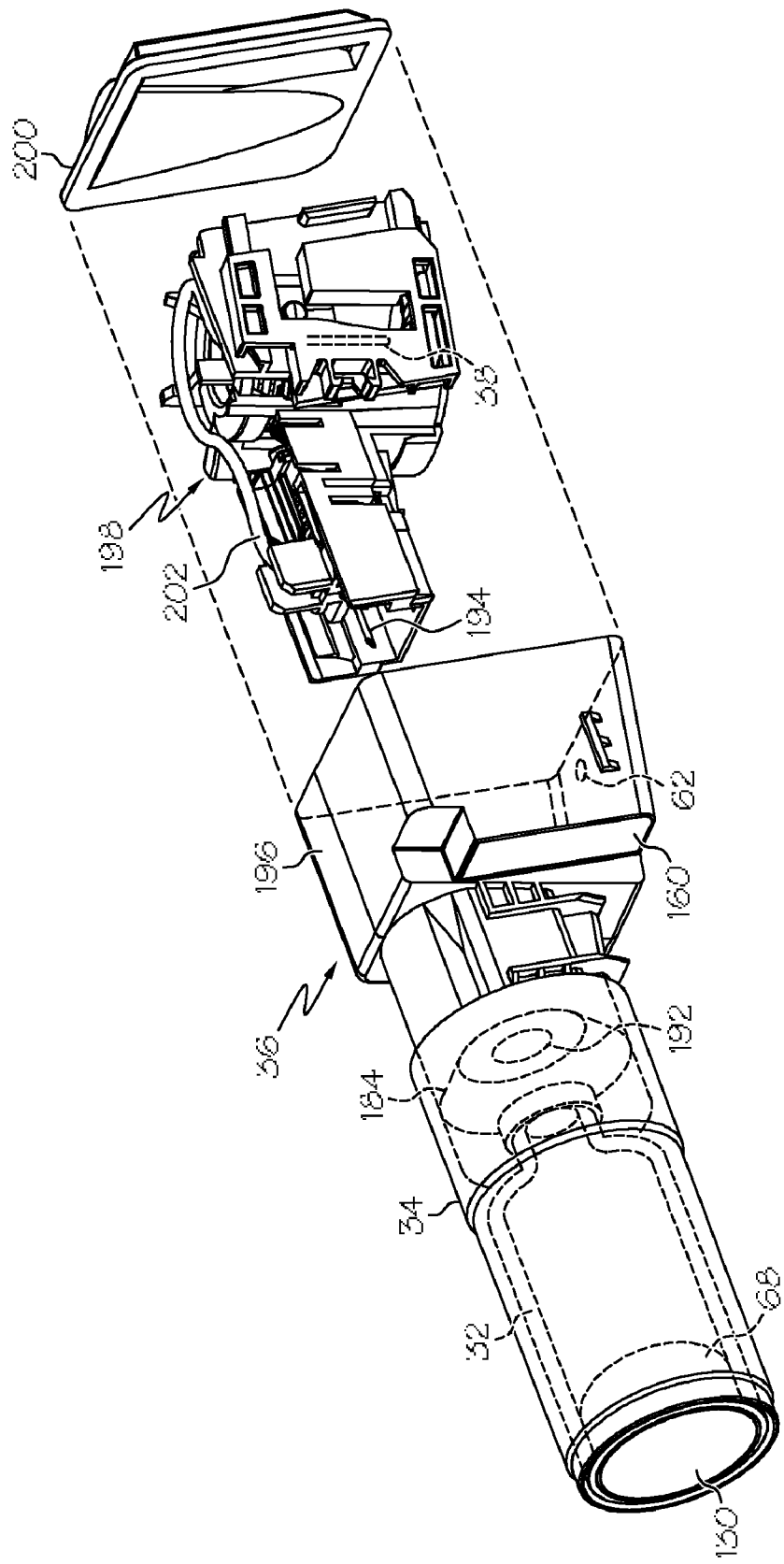
FIG. 13 is a partial exploded view of a transfer unit with a cartridge holder containing a cartridge according to an embodiment of the present invention.

With reference to FIG. 13, the transfer unit 36 comprises a transfer housing 196 that provides the docking port 184 which is shown connected with the cartridge holder 34. The transfer housing 196 also includes the sterile barrier 160 through which the piercing member 162 (FIG. 5) of the actuator unit 44 passes to trigger the extension and retraction of the hollow needle 38 as well as sterile barriers 62 and 192 provided over the respective ports. The transfer unit 36 also includes a transfer assembly 198, which is enclosed in the transfer housing 196 by a cover 200, which also helps to provide and maintain the sterile environment. In this manner, the transfer unit 36 provides the hollow needle 38 as well as the cartridge needle 194 in a sterile environment until the drug delivery process has started.

Upon being triggered by the actuator unit 44 passing the piercing member 162 of the push rod 154 through the sterile barrier 160 to engage and move a component (i.e., trigger slider 204) of the transfer assembly 198, the cartridge needle 194 will pass through the septum closure 132 to provide a fluid path or delivery conduit for the volume of drug in the cartridge 32 to the hollow needle 38. Further movement of the component (i.e., trigger slider 204) of the transfer assembly 198 by corresponding movement of the push rod 154 will then cause the transfer assembly 198 to extend the hollow needle 38 through the port that was previously covered by the sterile barrier 62 (FIG. 4) and beyond the housing 12 into the body of the user. Movement of the stopper 68 via corresponding movement of the plunger 126 (FIG. 5) thereafter, will cause the drug to flow into the cartridge needle 194 and to the hollow needle 38 via a delivery conduit which conveys the drug into the body of the user. In one embodiment, the delivery conduit comprises a tube 202 connected at a first end to cartridge needle 194 and at a second end to the hollow needle 38. In such an embodiment, the tube may be a plastic. In another embodiment, the tube 202 may be metallic and provide sharply tipped ends, where one tipped end acts as the hollow needle 38 and the other tipped end acts as the cartridge needle 194. It is to be appreciated that still further movement of the component (i.e., trigger slider 204) of the transfer assembly 198 by corresponding movement of the push rod 154, will then cause the transfer assembly 198 to retract the hollow needle 38 back into the transfer unit 36, thereby removing the hollow needle 38 from the body of the user. Further details concerning the configuration and operating of the transfer assembly 198 according to a preferred embodiment are provided hereafter in reference to FIGS. 14 and 15.

Figure 14:
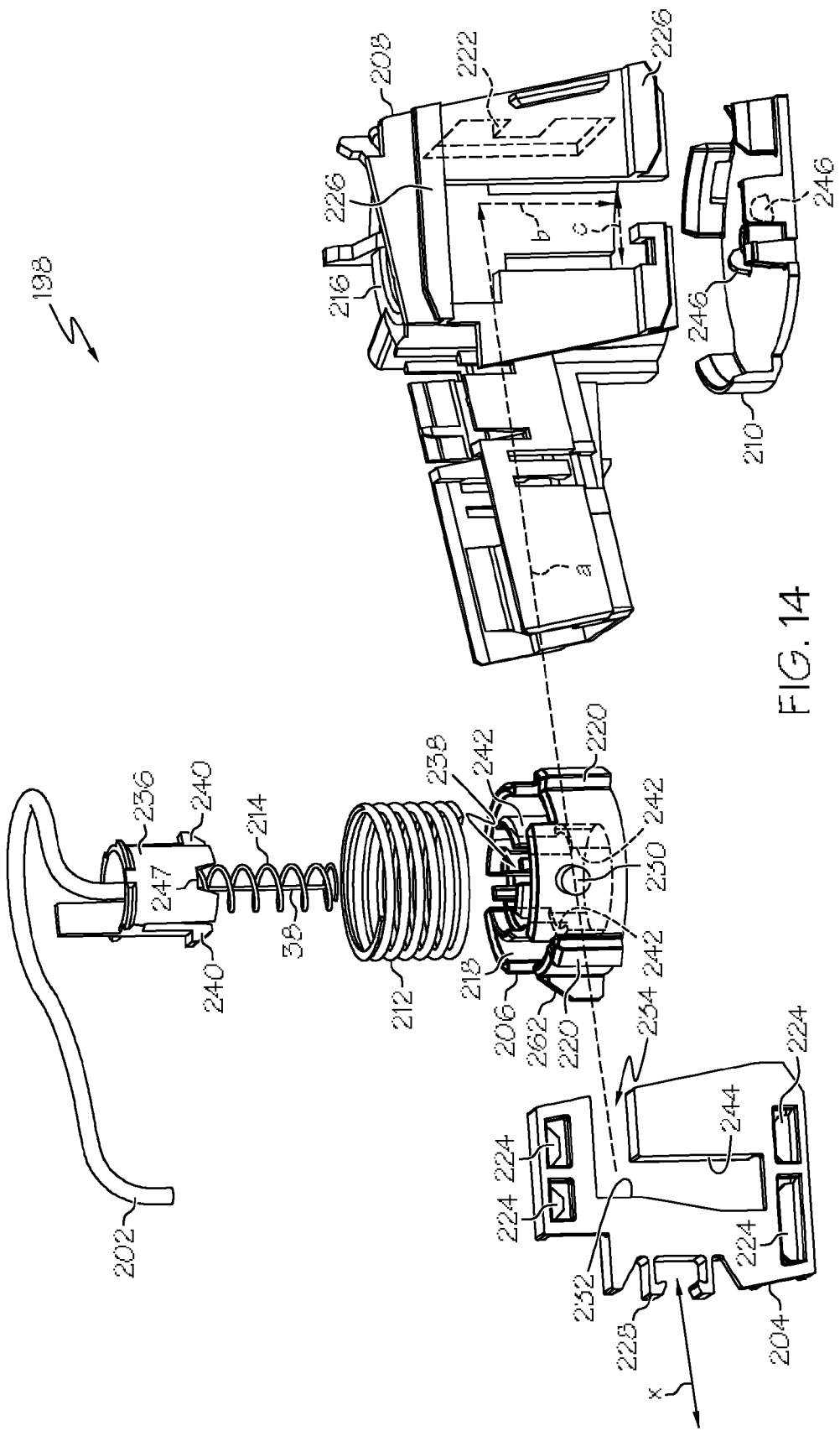
FIG. 14 is an exploded view of a transfer assembly of the transfer unit of FIG. 13 according to an embodiment of the present invention, the transfer assembly is partially cut away and shown with parts removed for convenience of illustration and discussion.
Figure 15:
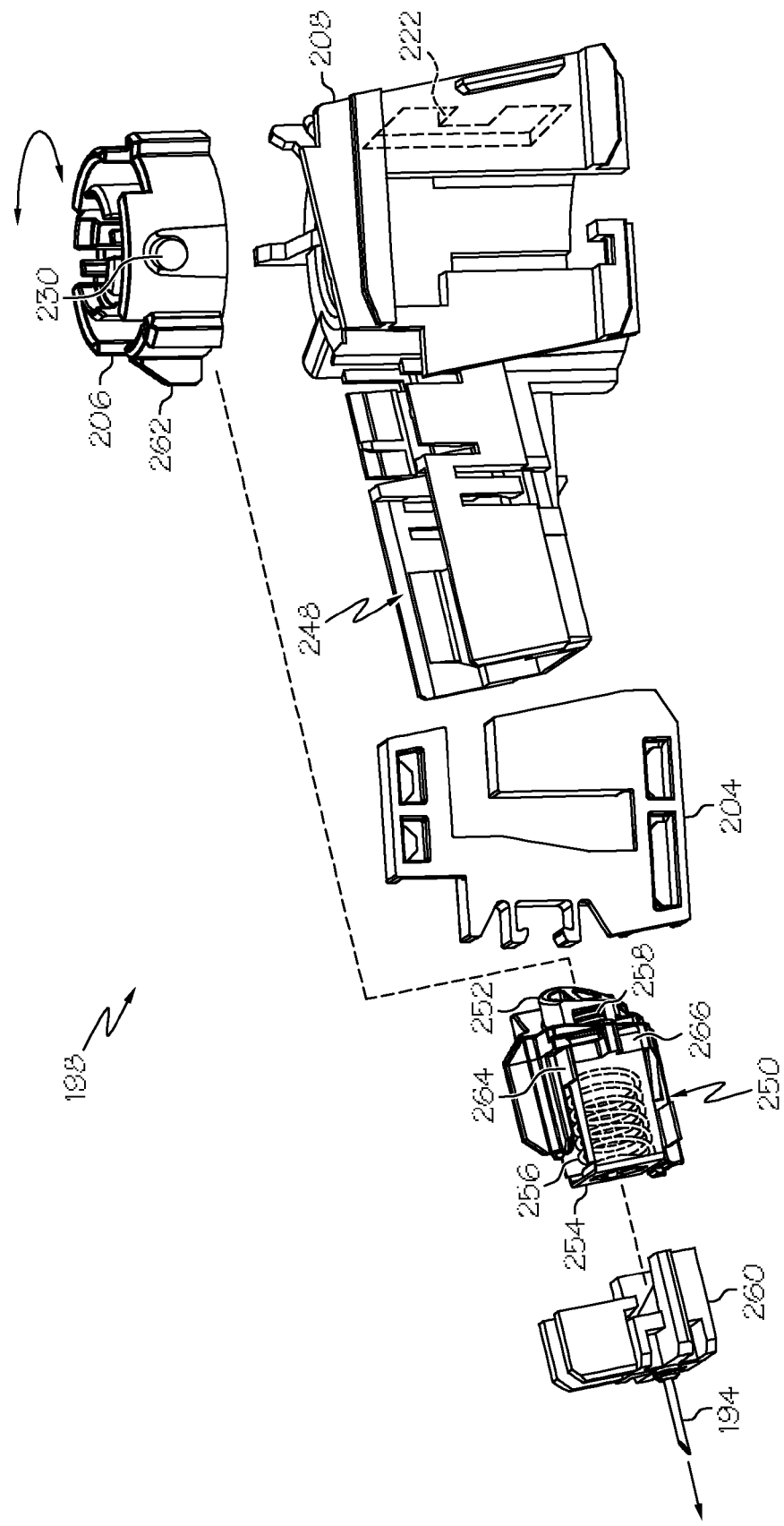
FIG. 15 is an exploded view of a transfer assembly of the transfer unit of FIG. 13 and showing the parts removed from FIG. 14, and having other parts removed for convenience of illustration and discussion.

FIGS. 14 and 15 each show the transfer assembly 198 in an exploded view and each figure having various components removed for ease of illustration and explanation. In particular, FIG. 14 shows a trigger slider 204, a trigger bushing 206, and a trigger housing 208 with a portion cut away. A cover 210 is provided to the bottom of the trigger housing 208 as well as first and second springs 212, 214. In a preferred embodiment, the first spring 212 is provided in the trigger housing 208 under compression in the initial, nonuse state of the device 10. When the actuator unit 44 triggers the transfer unit 36 (FIG. 5) to extend the hollow needle 38, the compression of the first spring 212 is released which compresses the second spring against the cover 210. The compression of the second spring 214 is then released when the actuator unit 44 triggers the transfer unit 36 to retract the hollow needle 38.

In a preferred embodiment, the first spring 212 in the initial, nonuse state of the device 10 is compressed against under an upper surface 216 of the transfer housing 208 by the trigger bushing 206. The trigger bushing 206 accommodates the first spring 212 in a channel 218 and maintains the compression of the first spring via tab portions 220 each engaging a respective landing 222 provided around the side of the transfer housing 208. The trigger slider 204 is slidably mounted to an exterior of the transfer housing 208 via hooked portions 224 of the trigger slider 204 slidably engaging a pair of spaced apart rails 226 of the transfer housing 208. The trigger slider 204 also provides a catch element 228 which captures the piercing member 162 (FIG. 5) after the piercing member 162 passes through the sterile barrier 160 (FIG. 13) of the transfer unit 36. In this manner, a firm connection is provided between the actuator unit 44 and the transfer unit 36, such that the trigger slider 204 will move with the piercing member 162 in both the first and second directions, which are indicated by the illustrated arrow designed by the symbol X. As the trigger slider 204 is moved in the first direction along the pair of rails 226, a torque arm 230 of the trigger bushing 206 is move by abutting against a wall portion 232 of a slot 234 provided in the trigger slider 204. As the wall portion 232 moves the torque arm 230, the torque arm 230 will transit along a path indicated by symbol A until the tab portions 220 clear their respective landing 222. Once the tab portions 22 clear their respective landing 222, the compression of the first spring 212 with be released, moving the trigger bushing 206 along the path indicated by symbol B to be adjacent to cover 210, thereby compressing the second spring 214 against the cover 210.

In the initial, non-used state of the device 10, the second spring 214 is mounted to a carrier 236 that provides the hollow needle 38. In the initial, non-use state of the device, the carrier 236 is releasably mounted to the trigger bushing 206 in a cavity 238 thereof via a snap-fit engagement between hook portions 240 of the carrier 236 and angled ramps 242 provided in the wall defining the cavity 238. In this initial condition, the second spring 214 extends from carrier 236 towards the cover 210 in an uncompressed state around the hollow needle 38 as shown by FIG. 14. When the trigger bushing 206 moves along path B under the force of the first spring 212, the carrier 236 will also be moved with trigger bushing 206. This is due to the snap-fit engagements between the hook portions 240 and the angled ramps 242. When the carrier 236 is situated adjacent to the cover 210 along with the trigger bushing 206, the hollow needle 38 is fully extended from the device 10.

As the trigger slider 204 is moved in the second direction along the pair of rails 226, the torque arm 230 of the trigger bushing 206 is moved again by abutting against another wall portion 244 of the slot 234 provided in the trigger slider 204. As the wall portion 244 moves the torque arm 230, the torque arm 230 will transit along a path indicated by symbol C, which rotates the trigger bushing 206 relative to the cover 210. It is to be appreciated that with the carrier 236 situated adjacent to the cover 210, a pair of protruding portions 246 of the cover 210 seat themselves into a respective notch 247 of the carrier 236. Thus, as the trigger bushing 206 rotates relative to the cover 210, the pair of notches 246 will hold the carrier 236 relative to the cover 210, thereby causing the hook portions 240 of the carrier 236 to disengage from the angled ramps 242 of the trigger bushing 206. Once the hook portions 240 are disengaged from the angled ramps 242, the compression of the second spring 214 is released, thereby retracting the hollow needle 38 back into the transfer housing 196.

Reference is now made to FIG. 15 in which a preferred embodiment for fluidly connecting the cartridge 32 with the hollow needle 38 is disclosed. FIG. 15 shows the complete trigger housing 208 providing a track portion 248. The track portion 248 supports and retains a firing mechanism 250 therein. The firing mechanism 250 includes a firing pin 252 that is spring biased towards the trigger bushing 206. The firing mechanism 250 further includes a clip 254 which is spring biased by a third spring 256 that is under compression in the initial, non-used state of the device 10. The spring bias of the firing pin 252 is provided by a fourth spring 258, which is also under compression in the initial, non-use state of the device 10. It is to be appreciated that the clip 254 is spring biased by a third spring 256 towards a shuttle 260 that provides the cartridge needle 194. In the initial, non-used state of the device 10, the shuttle 260 is situated in the track portion 248 such that the cartridge needle 194 is provided in the transfer housing 196 behind the sterile barrier 192 (FIG. 13). In addition, the end of the firing pin 252 is abutted against a protruding portion 262 of the trigger bushing 206, which provides the compression to the fourth spring 258. In this initial configuration, angled free ends of the clip 254 are each retained juxtaposed to a retainer 264 and a wall 266 of the firing pin 252 by an interference fit which retains the clip 254 and the compression of third spring 256. As the torque arm 230 transits along path A via movement of the trigger slider 204, the protruding portion 262 will clear its abutting engagement with the firing pin 252. Once the abutting engagement between the firing pin 252 and the protruding portion 262 is cleared, the firing pin 252 under force of fourth spring expanding, moves away from the retainer 264, thereby clearing the interference fit with the angled ends of the clip 254. With the interference fit cleared, the clip 254 under the force of the third spring expanding pushes the shuttle 260 down the track portion 248 with such force that the cartridge needle 194 passes through the sterile barrier 192 and the septum closure 132 (FIG. 12) of the cartridge 32. In one embodiment, the protruding portion 262 will clear its abutting engagement with the firing pin 252 before the tab portions 220 clear their respective landing 222 (FIG. 14). In such an embodiment, the process of extending the cartridge needle, extending and then retracting the hollow needle occurs sequentially. In other embodiments, the extending of the cartridge needle and the hollow needle may occur simultaneously.

Figure 16:
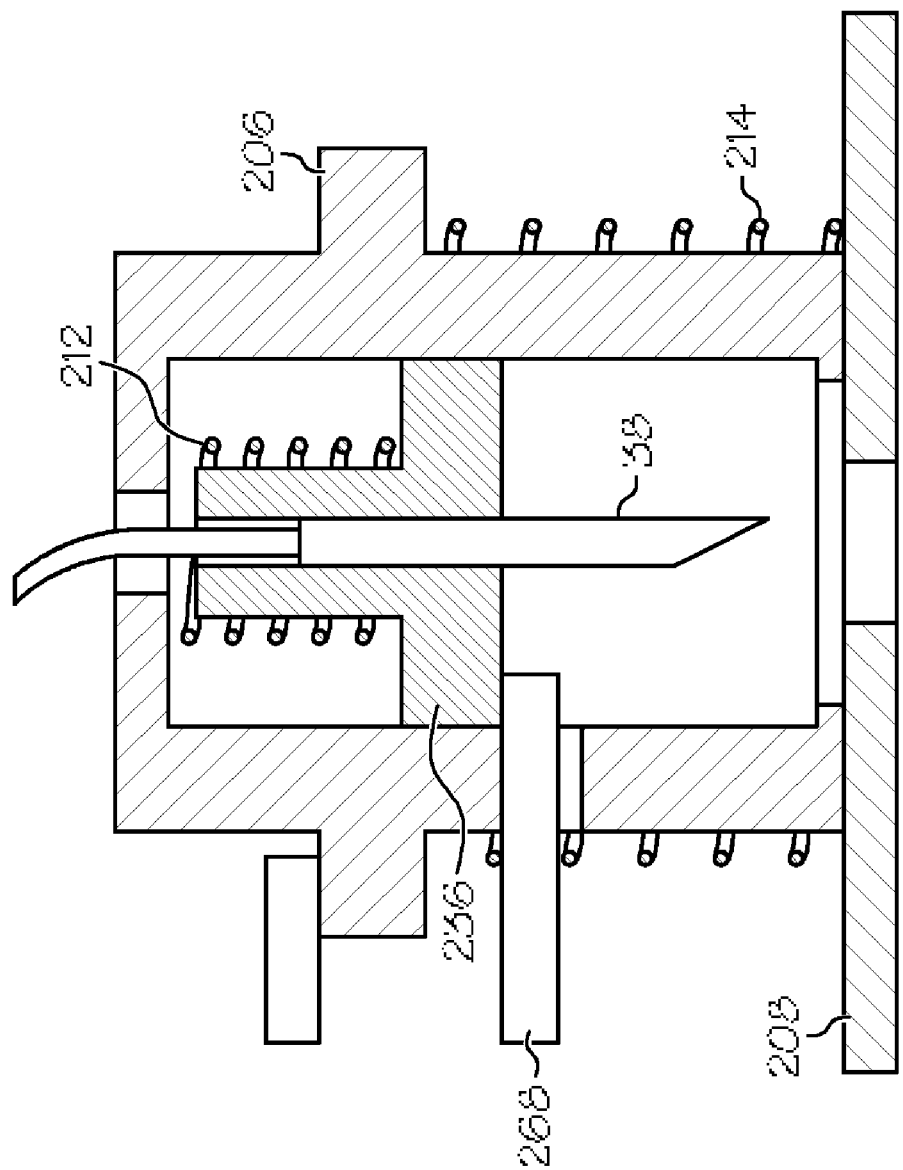
FIG. 16 is a cross-section schematic diagram of a transfer assembly of a transfer unit for a drug delivery device according to an other embodiment of the present invention.

With reference to FIG. 16, an alternative embodiment of extending and retracting the hollow needle 38 is provided. In this embodiment, the first and second springs 212, 214 are both provided in the trigger housing 208. In the initial, non-use state of the device 10, both springs 212, 214 are under compression. When the actuator unit 44 triggers the transfer unit 36 to extend the hollow needle 38, the compression of the first spring 212 is released by removing an interface fit between a first holding member 268 and the carrier 236. When the actuator unit 44 triggers the transfer unit 36 to retract the hollow needle 38, the compression of the second spring 214 is released by removing an interface fit between a second holding member 270 and the trigger bushing 206.

Figure 17:
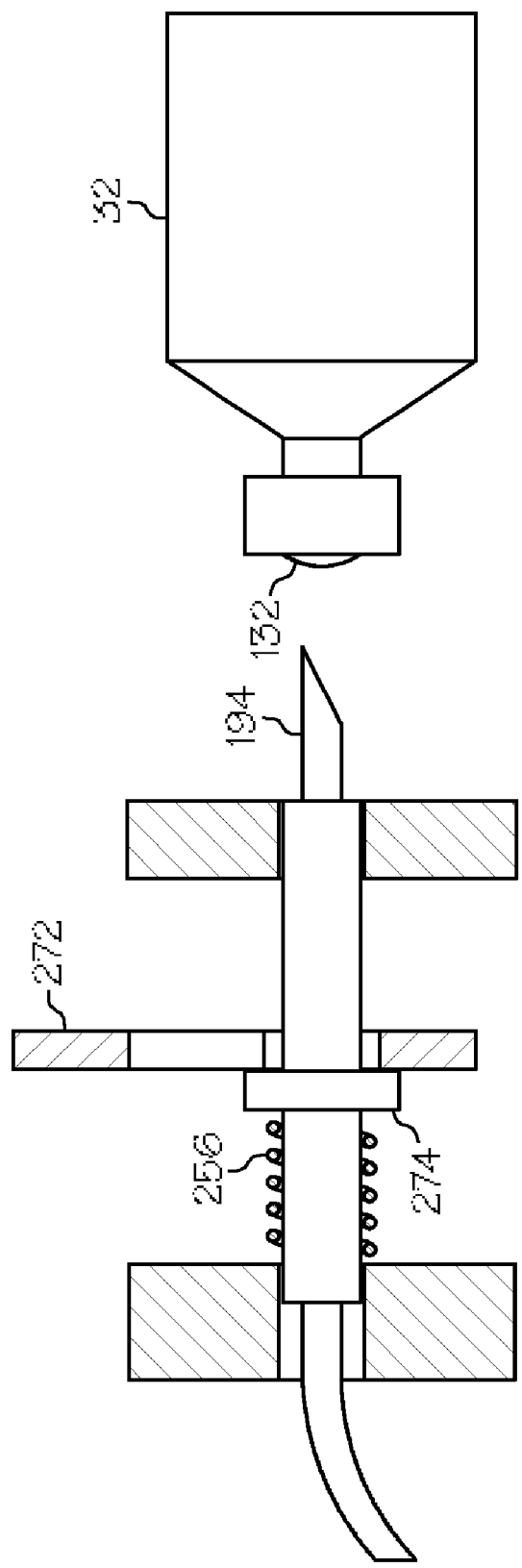
FIG. 17 is a cross-section schematic diagram of a cartridge injection assembly for a drug delivery device according to an embodiment of the present invention.

With reference to FIG. 17, an alternative embodiment of extending the cartridge needle is provided. In this embodiment, the third spring 256 in the initial, non-use state of the device 10, is under compression. When the actuator unit 44 triggers the transfer unit 36 to extend the cartridge needle 194, the compression of the third spring 256 is released by removing an interface fit between a holding member 272 and support 274 providing the cartridge needle 194. With the interference fit cleared, the support 274 under the force of the third spring 256 expanding, with send the cartridge needle 194 through at least the septum closure 132 of the cartridge 32.

Figure 18:
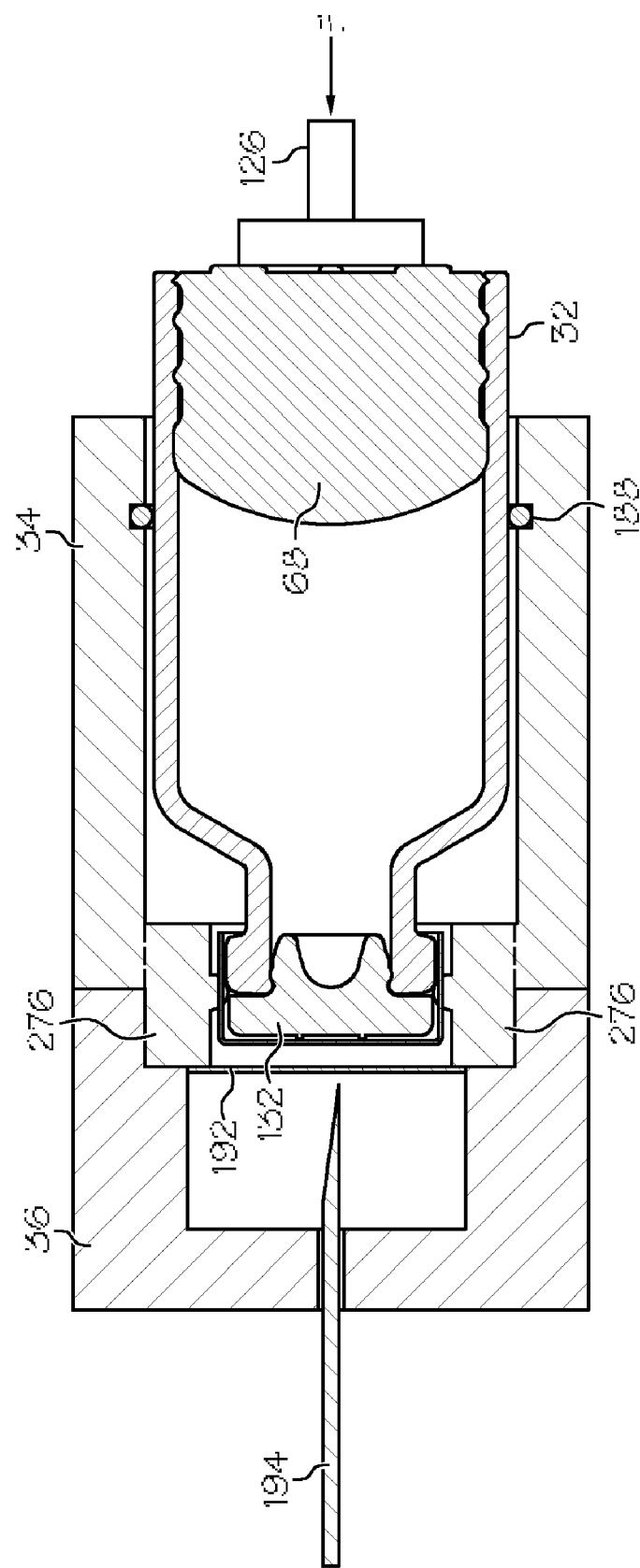
FIG. 18 is a cross-section schematic diagram of a cartridge injection assembly for a drug delivery device according to another embodiment of the present invention.

In still another embodiment such as shown by FIG. 18, the cartridge needle 194 is fixed, wherein the movement of the plunger 126 against the stopper 68 initially moves the cartridge 32 driving the cartridge needle 194 through the septum closure 132. In such an embodiment, a ringed support 276 may be provided by the interior surface of the cartridge holder 34 or separately such that the load force F is not carried by the head and neck portions 172, 174, but rather transferred to the transfer unit 36 during movement of the stopper 68. In addition, in still another embodiment, the O-ring 188 may be provided between the cartridge 32 and the cartridge holder 34 to help provide and maintain the aseptic environment. In such an embodiment, the cartridge holder 34 may be bonded to the transfer unit 36.

Electronic Control Unit

As shown in FIG. 5, the electronic control unit 40 comprises a microcontroller 278 that is electrically connected via the PCB 92 to the control switch 46, the LEDs 48, 48*a*, 48*b*, switch 90, electrical connectors 111, 122, wires 279 to motor 150, and switches 280*a*, 280*b*. As previously mentioned above, connectors 111 carry power to the control unit 40 from the battery 108, and connectors 122 supply power to the motor 112 of the drive unit 42 from the control unit 40. Similar connectors may also be used for wires 279 as well as wires for connectors 111 and 122. The power supplied to the motor 112 via connectors 122 and the power supplied to motor 150 via wires 279 is controlled by associated switches 280*a*, 280*b*, where are preferably field effect transistors (FETs). The switches 280*a*, 280*b* are individually operated by the microcontroller 278 programmatically according to the drug delivery process of the present invention.

The microcontroller 278 in a preferred embodiment is a single chip 8051 based microcontroller providing at least a CPU, program memory (RAM, ROM), I/Os, interrupt logic, oscillators, counters, converters, comparators, diagnostic self testing, and watchdog functions for power saving modes. In other embodiments, other microcontroller architectures, application specific integrated chip (ASIC), or the individual components provided by the microcontroller 278 may be used. The microcontroller 278 is also electrically connected via the PCB 92 to a number of discrete components (e.g., resistors, capacitors, transistors, diodes, etc.) 282 for configuration and functions which are discussed hereafter and in later sections.

The electronic control unit 40 controls the operational sequence of the drug delivery device 10 during the drug delivery process. The electronic control unit 40 interfaces with the start button 26 to start the drug delivery process via control switch 46, the status indicator 28 to give status of the drug delivery process, and the body sensor 24 to detect contact with the user's body. Generally, the electronic control unit 40 is configured such that after the start button 26 has been pressed for longer than the requisite amount of time, the electronic control unit 40 provides a ready-to-start status signal, e.g., a continuous green signal, via the microcontroller 278 powering the appropriate LED 48 as described to light the status indicator 28 if start-up checks provide no errors and in one embodiment also if body contact is indicated to the microcontroller 278 via a signal from the body sensor 24. The electronic control unit 40 is further configured to power down automatically if the start button 26 is released before the requisite amount of time. The electronic control unit 40 in another embodiment is further configured to power down automatically if after releasing the start button 26 no body contact is indicated to the microcontroller 278 by the body sensor 24. The advantage provided by the power down mode of the device 10 is in the event that the start button 26 is unintentionally pressed.

After the microcontroller 278 receives the ready to start signal, via the switch 46 being engaged by start button 26 for longer than the requisite amount of time and in one embodiment body contact is indicated by the body sensor 24, the control unit 40 will then command the actuator unit 44 to trigger the transfer unit 36 to automatically complete the fluid connection between the cartridge 32 and the hollow needle 28, and then to automatically extend the hollow needle 38 (FIG. 14) via the microcontroller 278 powering motor 150. In particular, the microcontroller 278 power the motor 150 by operating an associated switch 280*a* in a first manner such that the push rod 154 moves in a first direction which causes the above processes to be accomplished. After the hollow needle 38 has been injected, the control unit 40 next delivers the drug to the user by the microcontroller 278 powering motor 112 via operating an associated switch 280*b*, which moves the plunger 126 from an initial first position to a second position to dispense the drug from the cartridge 32. The control unit 40 will also provide a dispensing status signal, e.g., a flashing yellow signal of a first duration, via the microcontroller 278 powering the appropriate LED 48 as described to light the status indicator 28 during needle insertion and during delivery of the drug. In one embodiment, the microcontroller 278 will continue to provide the dispensing status signal during needle insertion and during delivery of the drug so long as the body sensor 24 continues to indicate contact with the body of the user to the microcontroller 278.

In a preferred embodiment, the control unit 40 controls the speed of both motors 112 and 150 by means of the microcontroller 278 receiving a back electromotive force measurement from the motors and processing the measurement in a motor control algorithm (e.g., PID) to provide corrections to the supply voltage, e.g., automatic change in PWM duty cycle, such that speed control is provided. It is to be appreciated that by controlling the speed of the motor 150, via the back emr-motor control algorithm, the control unit 40 detects insertion of the hollow needle 38. Insertion of the hollow needle 38 is detected by the microcontroller 278 being unable to keep the drive speed of the motor 150 on a certain nominal constant level (+/− tolerance) when the push rod reaches an end in the first direction, i.e., the torque arm 230 of the trigger bushing 206 abutting against the transfer housing 208 when on path B. In particular, if the microcontroller 278 cannot adjusted the drive speed of the motor 150 to its nominal value by a defined attempt period, the microcontroller 278 interprets this condition as the push rod 154 reaching the end of the first direction with the hollow needle 38 fully extended. Accordingly, the microcontroller 278 will then proceed to deliver the drug from the cartridge 32 by powering the motor 112 of drive unit 42 to move the plunger 126 from the first position to the second position.

Likewise, an end of cartridge detection is provided in a similar manner as to the needle insertion detection explained above. When the plunger 126 reaches its end, i.e., in the second position where the stopper 68 has closed the distance and is pushed to the cartridge neck portion 174 (FIG. 12), the drive speed of the motor 112 drops. In response, the microcontroller 278 tries to keep the drive speed of motor 112 on a certain nominal constant level (+/− tolerance) via adjusting the drive speed back to nominal speed i.e., increasing the PWM duty cycle. If the drive speed cannot be adjusted to its nominal value by a defined attempt period, the microcontroller 278 interprets this condition as end of cartridge. Accordingly, the microcontroller 278 will then proceed to finish the drug delivery process as explained hereafter.

After expiration of a dwell time, which is started and counted by the microcontroller 278 after detecting the end of the cartridge, the control unit 40 will command the actuator unit 44 to trigger the transfer unit 36 to retract the hollow needle 38. The hollow needle 38 is retracted via the microcontroller 278 powering motor 150 by operating the associated switch 280a in a second manner, e.g. reversing the applied motor voltage polarity, such that the push rod 154 moves in the second direction. It is to be appreciated that the dwell time is provided to ensure that there is no back-leakage of the medicine after being administered into the body of the user. In one embodiment, the dwell time used by the microcontroller 278 is about 10 seconds, and in other embodiments may be any time that is sufficient to ensure no back-leakage occurs for the medicine administered. The control unit 40 then detects needle retraction by the microcontroller 278 being unable to keep the drive speed of the motor 150 on a certain nominal constant level (+/− tolerance) when the push rod 154 reaches an end in the second direction. In one preferred embodiment, the end of the second direction is when the torque arm 230 of the trigger bushing 206 abuts against the transfer housing 208 when on path C. After failing to adjust motor speed to its nominal value by the defined attempt period, the microcontroller 278 interprets this situation as the push rod 154 reaching the end of the second direction with the hollow needle 38 retracted. After retraction detection, the control unit 40 will provide an okay-to-remove status signal, e.g., a continuous green signal, via the microcontroller 278 powering the appropriate LED 48 to light the status indicator 28 as described.

In one embodiment, after providing the okay-to-remove status signal and upon the body sensor 24 indicating non-contact with the body of the user to the microcontroller 278, e.g., upon removal, the control unit 40 will provide a remove battery signal, e.g., flashing green signal of the first duration via the microcontroller 278 powering the appropriate LED 48 to light the status indicator 28 as described. Also, in the embodiment with the body sensor 24, if at any time during the drug delivery process, the body sensor 24 indicates non-contact with the body of the user to the microcontroller 278 after initially indicating satisfactory body contact, e.g., body contact greater than 3 seconds, the control unit 40 will provide a first warning signal, e.g., alternating flashing yellow and green signal of the first duration. The first warning signal is provided via the microcontroller 278 powering alternatively the appropriate LEDs 48 to light the status indicator 28 as described. In the above situation, if the body sensor 24 continues to indicate no contact with the body of the user to the microcontroller 278 after a warning period, e.g., still no contact after 10 seconds, the control unit 40 will provide a second warning signal, e.g., flashing yellow of a second duration. The second warning signal is provided via the microcontroller 278 powering the appropriate LED 48 as described to light the status indicator 28. The second warning signal when provided indicates that an error has occurred in the device 10 and its further use discontinued. The second warning signal may also be provided if an error occurs during the self-test after being powered on. In one embodiment, the second duration of lighting the LED is different from the first duration. In still another embodiment, the second duration is less than the first duration. In one embodiment, the first duration is 600 ms, and the second duration is 200 ms.

System Behavior

Figure 19:
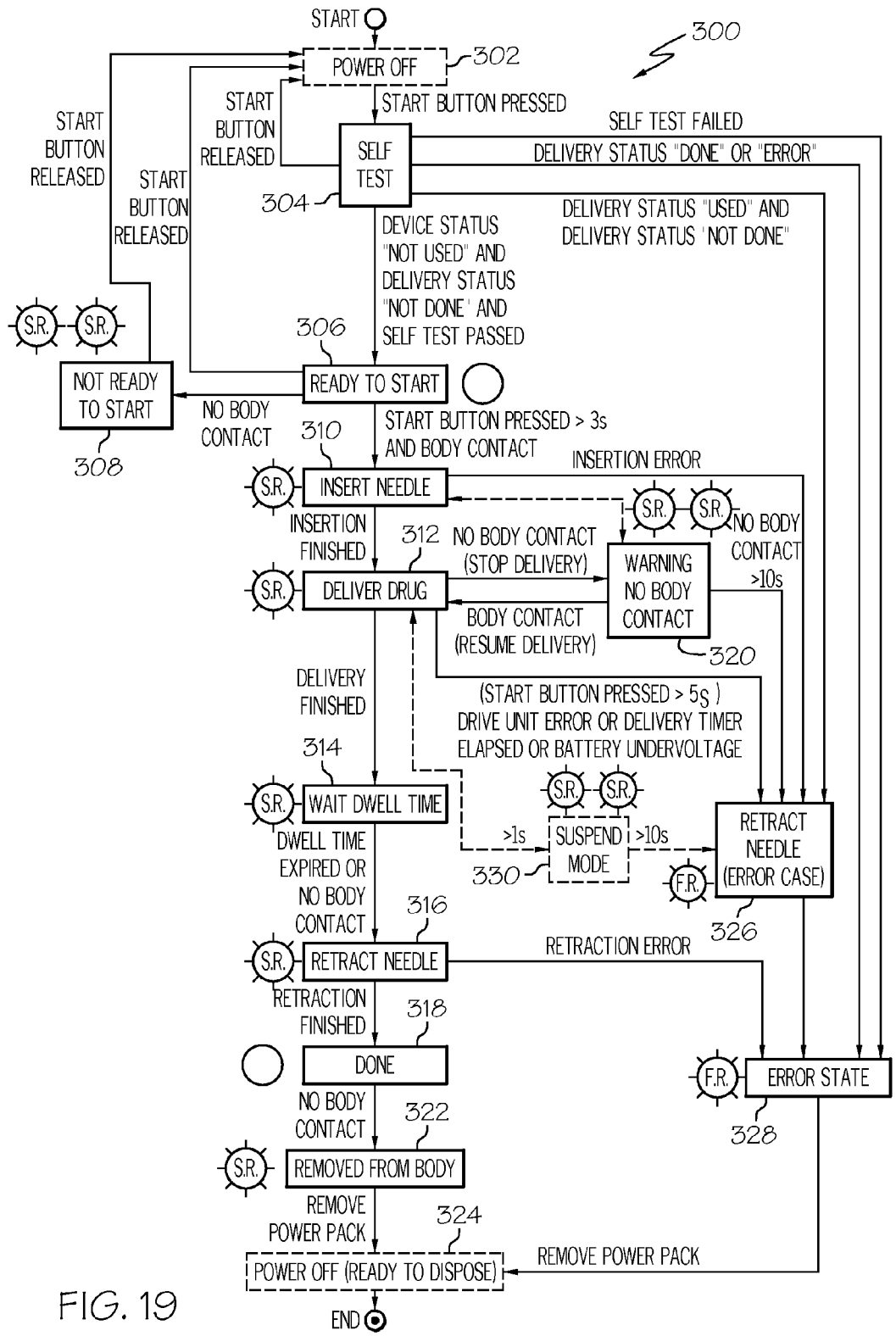
FIG. 19 is a flow chart depicting embodiments of a drug delivery process conducted by a drug delivery device according to the present invention.

With reference made to FIGS. 5 and 19, further embodiments of the drug delivery process 300 performed by the control unit 40 of the device 10 are disclosed. In particular, the flow diagram of FIG. 19 shows operating states and the transitions between the operating states along with specific system behavior of the device 10. As shown in FIG. 19, the different operating states of the device 10 in the preferred embodiment are as follows: POWER OFF 302, SELF TEST 304, READY TO START 306, NOT READY TO START 308, INSERT NEEDLE 310, DELIVER DRUG 312, WAIT DWELL TIME 314, RETRACT NEEDLE 316, DONE 318, WARNING NO BODY CONTACT 320, REMOVED FROM BODY 322, POWER OFF (READY TO DISPOSE) 324, RETRACT NEEDLE (ERROR CASE) 326, and ERROR STATE 328. POWER OFF 302 is the operating state after manufacturing of the device 10, e.g., the initial, non-used state. In this state, a non-volatile flag in memory of the control unit 40 is set to indicate to the microcontroller 278 upon powering up that the device 10 has not attempted to deliver the drug. After pressing the start button 26 (FIG. 5), the operating state of the microcontroller 278 changes automatically to SELF TEST 304 via receiving a signal from control switch 46.

SELF-TEST 304 is the operating state after the start button 26 has been pressed, wherein the microcontroller 278 executes the following actions. The microcontroller 278 checks that the power supply voltage from the battery 108 is suitable for conducting drug delivery process 300, and runs a program memory test, a data memory test, a CPU test, and a time based test to ensure that the control unit 40 is in a condition to conduct the remaining steps of the drug delivery process 300. In one embodiment, the processing of SELF-TEST 304 takes about 1000 millisecond (ms). If any of the processes in SELF-TEST 304 fail or if the non-volatile flag in memory of the control unit 40 is set to indicate to the microcontroller 278 that the device 10 has attempted to deliver the drug, the operating state of the microcontroller 278 will change automatically to ERROR STATE 328. In another embodiment, if the start button 26 is pressed and the body sensor 24 indicates body contact, and there is no error resulting from either the processes of the SELF-TEST 304 or the non-volatile flag, then the microcontroller 278 will change automatically its operating state to READY TO START 306. If, however, the start button 26 is pressed and the body sensor 24 indicates no body contact, the microcontroller 278 changes automatically the operating state to NOT READY TO START 308, wherein the first warning signal mentioned previously above is provided. If body contact in the operating state NOT READY TO START 308 is not indicated by the body sensor 24 then in one embodiment when the start button 26 is released the microcontroller 278 will switch off the power supply, thus changing automatically the operating state to POWER OFF 302. In another embodiment in which the start button is provided with a timeout, if after completion of the start command, e.g., releasing of a start button, whereby body contact is not indicated by the body sensor 24 within a delay period, e.g. 5 seconds, then the microcontroller 278 will change automatically to the operating state POWER OFF 302.

The microcontroller 278 enters the READY TO START 306 operating state when the processes in SELF TEST 304 are successful, the non-volatile flag indicates the device 10 has not previously attempted to dispense the drug, and the body sensor 24 indicates body contact. In this operating state, the microcontroller 278 provides the ready-to-start status signal, e.g. continuous green signal. In this state, the microcontroller 278 waits until simultaneously the start button 26 is pressed for more than the requisite amount of time (e.g., 3 seconds) and the body sensor 24 indicates body contact. After those two conditions are met, the microcontroller 278 will then change automatically the operating state to INSERT NEEDLE 310 and set in memory the non-volatile flag to indicate a delivery attempt.

During the operating state INSERT NEEDLE 310, the hollow needle is inserted automatically below the skin of the user by the device 10 as previously discussed above. In addition, during this operating state, the microcontroller 278 will provide the dispensing status signal, e.g., a flashing yellow signal of a first duration, as mentioned previously above. It is to be appreciated that during the operating state INSERT NEEDLE 310, the microcontroller 278 monitors the motor 150 of the actuator unit 44 for an indicated change in its operating condition. If the motor 150 fails to start, such as for example, due to an open electrical circuit or mechanical block, or does not stop after a run period, thus indicating mechanical slip, the microcontroller 278 will change automatically the operating state to RETRACT NEEDLE (ERROR CASE) 326. In one embodiment, the run period is about 5 seconds and in other embodiments, shorter or longer run periods may be used. In one embodiment, if at any time during the operating state INSERT NEEDLE 310 the body sensor 24 fails to indicate body contact to the microcontroller 278, the microcontroller 278 can change automatically the operating state to WARNING NO BODY CONTACT 320. If the body sensor 24 within a delay period does not indicate body contact in the operating state WARNING NO BODY CONTACT 320, e.g. within 10 seconds, the microcontroller 278 will change automatically the operating state to RETRACT NEEDLE (ERROR CASE) 326. Otherwise, if the body sensor 24 within the delay period indicates body contact in the operating state WARNING NO BODY CONTACT 320, the microcontroller 278 will change automatically the operating state back to the operating state INSERT NEEDLE 310. After the microcontroller 278 detects the automatic insertion of the hollow needle 38 into the body of the user as mentioned previously above, the microcontroller 278 then changes automatically the operating state to DELIVER DRUG 312.

DELIVER DRUG 312 is the operating state when the drug is dispensed automatically from the cartridge 32 by the microcontroller 278 powering the motor 112 of drive unit 42 to move the plunger 126 at a constant speed until the full cartridge content has been administered as signaled via the end of cartridge detection as previously explained above. During this operating state, the microcontroller 278 will continue to provide the dispensing status signal, e.g., the flashing yellow signal of the first duration, as mentioned previously above. It is to be appreciated that during the operating state DELIVER DRUG 312, the microcontroller 278 monitors the motor 112 of the drive unit 42 for an indicated change in its operating condition. One of the cases monitored for a change in operating condition is if the motor 112 fails to start, such as for example, due to an open electrical circuit or mechanical block. Another case is if the motor 112 does not stop after a drug administration time, thus possibly indicating mechanical slip. Still another case is if the microcontroller 278 is unable to keep the drive speed of the motor 112 on the certain nominal constant level within 25% of a nominal run time of the shortest cartridge useable with the device, thus indicating a possible delivery conduit blockage. Yet another case is if a battery undervoltage is detected by the microcontroller 278., On occurs of any of such cases the microcontroller 278 will change automatically the operating state to RETRACT NEEDLE (ERROR CASE) 326, stopping the motor 112 and attempting to retract the needle 38 as well as provide an error signal e.g., a quick flashing yellow signal (e.g., 200 ms on/200 ms off). In one embodiment, the above mentioned drug administration time is a nominal run time of the longest cartridge useable with the device plus a safety margin (e.g., 25%), and in other embodiments, shorter or longer drug administration times or other safety margins may be used. It is to be appreciated that the drug administration time is the same for all cartridge volumes as the drive speed of the plunger 126 provided by the drive unit 42 is constant and is the same for all cartridge lengths. In addition, if at any time during the operating state DELIVER DRUG 312 the body sensor 24 fails to indicate body contact to the microcontroller 278, the microcontroller 278 will change automatically the operating state to WARNING NO BODY CONTACT 320 and automatically stop the deliver process, i.e. administering the drug. If the body sensor 24 within a delay period does not indicate body contact in the operating state WARNING NO BODY CONTACT 320, e.g. within 10 seconds, the microcontroller 278 will change automatically the operating state to RETRACT NEEDLE (ERROR CASE) 326. Otherwise, if the body sensor 24 within the delay period indicates body contact in the operating state WARNING NO BODY CONTACT 320, the microcontroller 278 will change automatically the operating state back to the operating state DELIVER DRUG 312 and resume the delivery process, i.e. resume the administering of the drug. After end of cartridge detection, the microcontroller 278 changes the operating state automatically to WAIT DWELL TIME 314.

WAIT DWELL TIME 314 is the operating state after the desired volume of the cartridge is indicated as being administered via the microcontroller 278 detecting the end of cartridge. As mentioned previously above, the dwell time is the waiting time before the hollow needle 38 is retracted from the body of the user to ensure no back seepage of the administered drug. During this operating state, the microcontroller 278 will continue to provide the dispensing status signal, e.g., the flashing yellow signal of the first duration, as mentioned previously above. During this operating state, if either after expiration of the dwell time via a counter started by the microcontroller 278 after the end of cartridge detection or no body contacted is indicated by the body sensor 24 to the microcontroller 278, the operating state will changed automatically to RETRACT NEEDLE 316 by the microcontroller 278.

RETRACT NEEDLE 316 is the operating state when the hollow needle 38 is automatically retracted from the body of the user by the device 10 as explained previously above. During this operating state, the microcontroller 278 will continue to provide the dispensing status signal, e.g., the flashing yellow signal of the first duration, as mentioned previously above, and monitor the motor 150 of the actuator unit 44 for an indicated change in its operating condition. If the motor 150 fails to start, such as for example, due to an open electrical circuit or mechanical block, or does not stop after a run period, thus indicating mechanical slip, the microcontroller 278 will change automatically the operating state to ERROR STATE 328. After the hollow needle 38 is detected as being retracted from the body of the user by the microcontroller 278 as also explained previously above, the microcontroller 278 then automatically changes the operating state to DONE 318.

DONE 318 is the operating state after the hollow needle is retracted from the body of the user back into the house 12 of the device 10. In this operating state, the microcontroller 278 provides a finished status signal, e.g. continuous green signal, and waits for the body sensor 24 to provide a no body contact indication. Once the no body contact indication is provided, the microcontroller 278 automatically changes its operating state to REMOVED FROM BODY 322.

REMOVE FROM BODY 322 is the operating state after the drug delivery device 10 is removed from the body of the user. In this operating state, the microcontroller 278 provides either an okay-to-dispose signal, e.g., green flashing signal (600 ms on/600 ms off) or quick flashing yellow signal (e.g., 200 ms on/200 ms off) if following the operating state ERROR STATE 328. The okay-to-dispose signal continues until the power pack 18 is removed from the device or the charge on the battery 108 drains. Once the power pack 18 is removed, the operating state by default becomes POWER OFF (READY TO DISPOSE) 324, wherein the device 10 is rendered inoperable and can be disposed in a normal manner with the power pack being place in an appropriate bin for recycling.

RETRACT NEEDLE (ERROR CASE) 326 is the operating state after an error has occurred at any time during the drug delivery process 300. If the microcontroller 278 enters into this operating state, the microcontroller 278 will provide an error signal, e.g., a quick flashing yellow signal (e.g., 200 ms on/200 ms off), automatically stop the motor 112 to the drive unit 42, and attempt to retract the hollow needle 38. After these steps, the microcontroller 378 will automatically change the operating state to ERROR STATE 328.

ERROR STATE 328 is the state in which an error has occurred in one of the previous step. Once in the ERROR STATE 328 a delivery status flag is set to done or error in memory of the microcontroller 278 such that the device 10 cannot be used again. While in the ERROR STATE 328, the microcontroller 278 will provide an error signal, e.g., a quick flashing yellow signal (e.g., 200 ms on/200 ms off) until the power pack 18 is removed from the device 10 or the charge on the battery 108 drains.

In an alternative embodiment without the body sensor 24, the operating states NOT READY TO START 308, WARNING NO BODY CONTACT 320, and REMOVED FROM BODY 322 can be omitted in the drug delivery process 300. In still another alternative embodiment, after pressing the start button 26, the device 10 goes to the READY TO START 306 and waits in order to avoid unintended use. The drug delivery process 300 at this point has to be confirmed again by the user pressing the start button 26 for greater than the requisite time in order to proceed to INSERT NEEDLE 310. In one embodiment, if the start button 26 is not pressed by elapse of a wait period (e.g., 30 seconds) counted by the microcontroller 278, the device 10 returns automatically to the POWER OFF 302.

In yet another embodiment, an emergency shutdown feature is provided. If the start button 26 is pressed by the user for more than 5 seconds during the DELIVERY DRUG 312 state, the microcontroller 278 will stop administering the drug and automatically proceed to RETRACT NEEDLE (ERROR CASE) 326 to retract the needle and then to the POWER OFF (READY TO DISPOSE) 324 to power off. In still another embodiment, a SUSPEND MODE 330 may be provided in which a press of the start button 26 which falls within a time window e.g., longer than a second but shorter than ten seconds, while in the DELIVER DRUG 312 state will cause the microcontroller 278 to temporarily stop the administering of the drug. The microcontroller 278 in this embodiment will resume the administering the drug upon the start button 26 being pressed again for a period that falls within the time window. If however, the start button is pressed for a period longer then the upper end of the time window (e.g., >10 seconds) then the microcontroller 278 automatically processed to RETRACT NEEDLE (ERROR CASE) 326 to retract the hollow needle 38 and then to the POWER OFF (READY TO DISPOSE) 324 state to power off. In still another embodiment, a dedicated panic button 99 (FIG. 4) can also be located on the bottom housing 22 and used to stop the drug delivery process immediately, retract the hollow needle 38 and go to the power off state.

Use Case

Figure 20A:
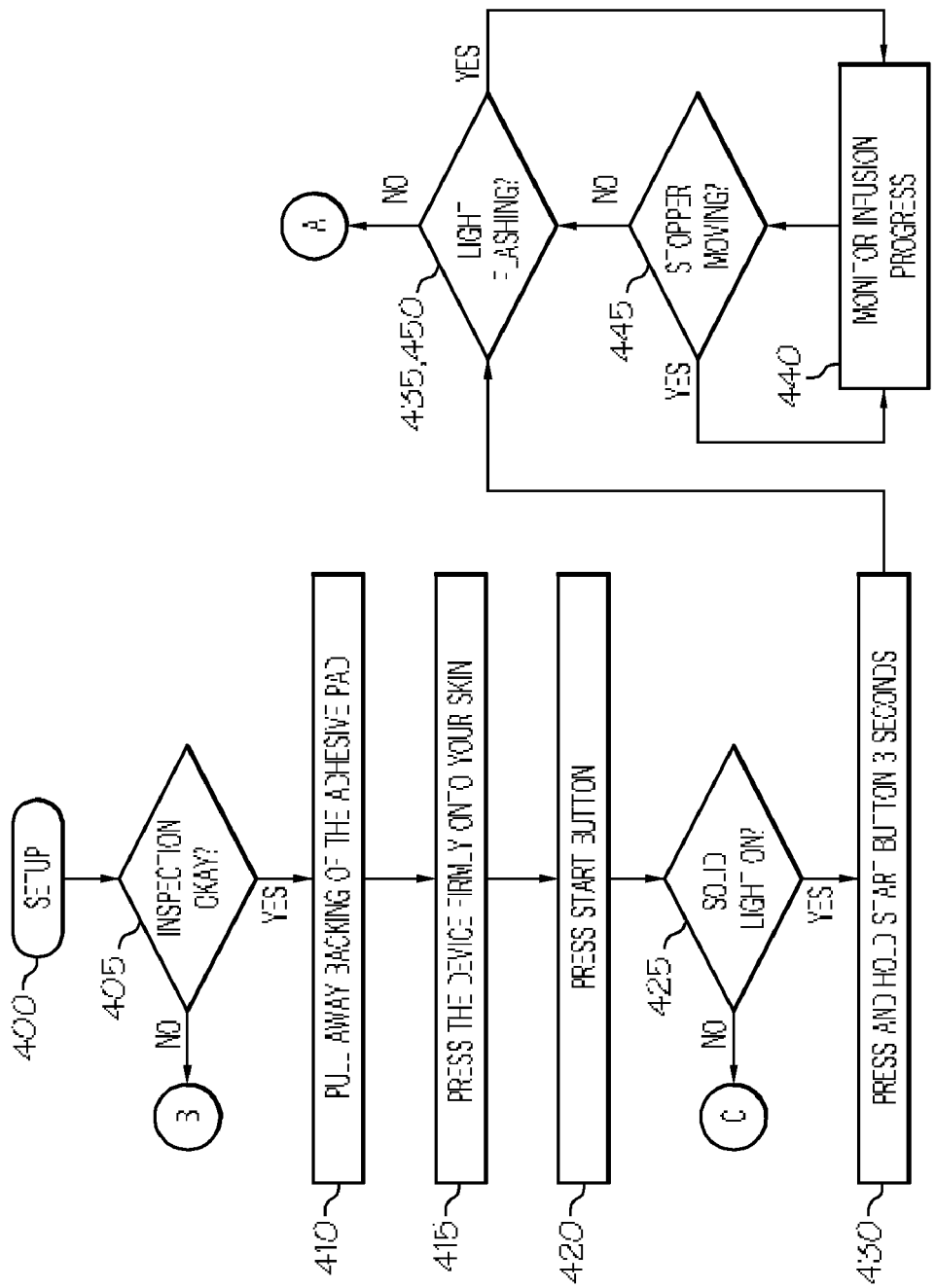

A method of administering (infusing/injecting) medication utilizing the device 10 according to a preferred embodiment is now explained hereafter with reference made to FIGS. 20A and 20B. In step 400, a user/patient setups for the use of the device 10. Setup can include actions such as hand washing hands before opening the packaging and handling the device 10, checking through the window 30 for obvious signs of damaged to the cartridge 32 or indications that the medication does not look normal e.g. contains lumps or sediment. In addition, setup can include checking a label 31 on the device 10 to see that the medication has not expired, and preparing an insertion site for the device, e.g., abdomen or thigh. If in step 405 the inspection checks are okay, then in step 410, the user prepares the device for use by pulling away the liner 56 of the adhesive layer 54. Next, in step 415 the user places the device 10 onto the body at the prepared site. For example, the user will press the device firmly onto the skin and run a finger around the adhesive material (pad) 54 to make sure that it sticks well. Next, in step 420, the user starts the drug delivery process 300 (FIG. 19) by turning on the device 10 via pressing and holding the start button 26. While pressing the start button 26, the user then checks in step 425 the status indicator 28 for a solid light. If a solid light is provided by the status indicator 28, then in step 430 the user will continue to press and hold the start button 26 for a period, e.g., >3 seconds. In step 435, the user can then check to see whether a flashing light has come on. If so, then in step 440 the user can monitor the drug delivery process by occasionally checking to see if the stopper 68 is move in the window in step 445 and/or whether the status indicator 28 is providing a flashing light in step 450. If step 445 and 450 are negative then in step 455 (FIG. 20B) the user checks to see that a solid light is provided by the status indicator 28 or waits 10 seconds. Next, in step 460, the user cleans up by pulling on the loop 60 of the adhesive layer 54 away from the body to remove the device 10. This step would also occur, if in step 425 no solid light was provided via no body contract or an error. In such case, either the first warning signal i.e., no body contact detected or the second warning signal i.e., error state, would be provided. Next in step 465, the user removes the power pack 18 from the device 10. This step should occur after the device 10 has provided a flash signal on the status indicator 28. In step 470, the user puts the power pack 18 in a recycling bin and throws the device 10 away as normal rubbish.

Advantages

Some of the noted advantages, and not limited thereto, of the above mentioned embodiments of the present invention are as follows. Users can use the device 10 at home by themselves. Visibility is improved via the flashing and constant LED modes as the user only needs to glance down at the status indicator 28 when the device is attached rather than having to watch continuously the plunger in a window 30. In addition, accessibility is improved due to the location of the start button 26 on the housing top 20 such that the start button 26 can be pressed with all digits and even a knuckle if hand motor skills of the user are particularly bad. Furthermore, the body sensor 24 and the adhesive layer 54 can provide assurances that the devices had been positioned and orientated correctly, thus improving user confidence in knowing that the device will be used correctly. In addition, audible feedback and tactile feedback is provided via operation of the motors 112, 150 as well as the ability to have the battery 108 recycled via the power pack 18 being easily removable from the device 10 after use.

It is noted that terms like "preferred", "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention, it is noted that the terms "approximately" and "about" are utilized herein to represent the inherent degree of uncertainty that may be attributed to any quantitative comparison, value, measurement, or other representation. The terms "approximately" and "about" are also utilized herein to represent the degree by which a quantitative representation may vary from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. A drug delivery device for pumping medication into the body of a user, the device comprising:
 a housing having a start button and a status indicator;
 a cartridge holder having a sterile barrier at a first end thereof and arranged in the housing;
 a cartridge containing a volume of the medication to be dispensed;
 a drive unit having a plunger, the plunger being movable from a first position adjacent the sterile barrier to a second position in which the plunger has moved through the sterile barrier by piercing the sterile barrier and the plunger has dispensed the volume of the medication from the cartridge;
 a transfer unit providing a delivery conduit for the volume of medication from the cartridge to an included hollow needle, the transfer unit being connected to a second end of the cartridge holder and together providing an aseptic environment for the cartridge, the transfer unit being configured to extend the hollow needle beyond the housing and retract the hollow needle back into the housing after the hollow needle has been extended and the medication has been dispensed from the cartridge; and
 an electronic control unit which controls the drive unit, and interfaces with the start button and the status indicator, the electronic control unit being configured such that after the start button has been pressed longer than a requisite amount of time, the electronic control unit causes the transfer unit to extend the hollow needle and powers the drive unit such that the plunger moves from the first position to the second position.

2. The drug delivery device of claim 1 wherein the transfer unit has a cartridge needle for passing through a septum closure of the cartridge and fluidly connected to the hollow needle.

3. The drug delivery device of claim 1 wherein the transfer unit has a second sterile barrier which provides a sterile environment for the hollow needle within the transfer unit.

4. The drug delivery device of claim 1 further comprising an actuator unit which triggers the transfer unit to extend the hollow needle when caused to move in a first direction by the control unit and to retract the hollow needle when caused to move in a second direction by the control unit.

5. The drug delivery device of claim 1 wherein the electronic control unit after expiration of a dwell period further causes the transfer unit to retract the hollow needle when the plunger is at the second position and provides an okay-to-remove status signal via the status indicator after the hollow needle is retracted.

6. The drug delivery device of claim 1 further comprising a body sensor and wherein the electronic control unit causes the transfer unit to extend the hollow needle and powers the drive unit such that the plunger moves from the first position to the second position if the body sensor indicates contact with the body of the user to the control unit.

7. The drug delivery device of claim 1 wherein the electronic control unit provides a dispensing status signal via the status indicator when the plunger moves from the first position to the second position.

8. The drug delivery device of claim 1 wherein the housing further includes a window, and the cartridge has a movable stopper that is viewable through the cartridge holder and the window of the housing.

9. The drug delivery device of claim 1 wherein the housing is formed of top and bottom portions connected together, and a window is provided on a side formed between the top and bottom portions.

10. The drug delivery device of claim 1 wherein the housing is formed of top and bottom portions connected together, wherein the top portion provides the start button and the status indicator.

11. The drug delivery device of claim 1 wherein the housing is formed of top and bottom portions connected together, wherein the bottom portion provides a body sensor.

12. The drug delivery device of claim 1 wherein the cartridge holder comprises a transparent tube providing the sterile barrier at the first end.

13. The drug delivery device of claim 1 wherein the cartridge holder has a movable support which supports a neck portion of the cartridge from movement therein.

14. The drug delivery device of claim 1 wherein the aseptic environment for the cartridge is provided by the sterile barrier at the first end of the cartridge holder and a substrate to substrate firmly bonded connection between the docking port (184) of the transfer unit and the cartridge holder.

15. The drug delivery device of claim 1 wherein the plunger is linearly displaced.

16. The drug delivery device of claim 1 wherein the plunger provides a piercing surface (128).

17. The drug delivery device of claim 1 wherein the plunger is a lead-screw driven by a gear set connected to a motor, and has a flange.

18. The drug delivery device of claim 2 wherein the cartridge needle is fixed to the transfer unit and passes through a septum closure of the cartridge by the plunger moving the cartridge towards the transfer unit after breaking through the sterile barrier.

19. The drug delivery device of claim 2 wherein the cartridge needle of the transfer unit is configured to pass through a septum closure of the cartridge via a spring force.

20. The drug delivery device of claim 4 wherein the transfer unit has first and second springs, the first spring being under compression and the second spring not being under compression in a non-use state of the device, wherein when the actuator unit triggers the transfer unit to extend the hollow needle the compression of the first spring is released compressing the second spring, and wherein the compression of the second spring is then released when the actuator unit triggers the transfer unit to retract the hollow needle.

21. The drug delivery device of claim 4 wherein the transfer unit has first and second springs both under compression, the compression of the first spring being released when the actuator unit triggers the transfer unit to extend the hollow needle, and the compression of the second spring being released when the actuator unit triggers the transfer unit to retract the hollow needle.

22. The drug delivery device of claim 21 wherein a cartridge needle is configured to pass through a septum closure of the cartridge via a third spring which is also under compression, the compression of the third spring being released when the actuator unit moves in the first direction but before the hollow needle is extended.

23. The drug delivery device of claim 22 wherein the second spring is mounted to a carrier which engages protruding portions of the transfer unit when the compression of the first spring is released such that the carrier can resist a torque provided by the actuator unit when moving in the second direction, thereby causing a catch element to be released to cause the compression of the second spring to be released.

24. The drug delivery device of claim 4 wherein the actuator unit comprises a motor, a push rod and gears, the motor turns the gears to drive the push rod which triggers the transfer unit to extend the hollow needle when driven in the first direction and triggers the transfer unit to retract the hollow needle when driven in the second direction.

25. The drug delivery device of claim 24 wherein the motor turns the gears to drive the push rod through a second sterile barrier of the transfer unit in the first direction to trigger the transfer unit to extend the hollow needle.

26. The drug delivery device of claim 6 wherein the body sensor comprises a switch which send a signal to the electronic control unit in a condition selected from an engaged condition and a disengaged condition.

27. The drug delivery device of claim 26 wherein the switch is a single pole, single throw microswitch.

28. The drug delivery device of claim 6 wherein the drive unit includes a motor which is automatically stopped if the body sensor sends a signal to the electronic control unit indicating no body contact.

29. The drug delivery device of claim 6 wherein the electronic control unit comprises a LED and phototransistor pair to create a light beam switch, wherein the body sensor in a pressed condition cause a condition selected from breaking a light beam between the LED and phototransistor pair to signal device contact with the body of the user to the electronic control unit and permitting a light beam to pass between the LED and phototransistor pair to signal device contact with the body of the user to the electronic control unit.

30. The drug delivery device of claim 6 wherein the body sensor include a magnet and the electronic control unit include a reed switch which causes a condition selected from opening the reed switch in the presence of the magnet when the body sensor is pressed to signal device contact with the body of the user to the electronic control unit and closing the reed switch in the presence of the magnet when the body sensor is pressed to signal device contact with the body of the user to the electronic control unit.

31. The drug delivery device of claim 1 wherein the start button contacts an electromechanical switch of the electronic control unit.

32. The drug delivery device of claim 1 further comprising a power pack providing power to the device, the power pack being removable from the housing.

33. The drug delivery device of claim 1 further comprising an adhesive layer for attaching the device to the body of the user; and a release liner for protecting the adhesive layer in a non-use condition, wherein removing the release liner from the adhesive layer also removes a sterile cover of transfer unit.

34. The drug delivery device of claim 1 wherein the status indicator comprises a light pipe in the form of a translucent ring provided around the start button.

35. The drug delivery device of claim 1 wherein the status indicator comprises a light pipe and LEDs, and the LEDs provide a constant light to the light pipe for both the ready-to-start status signal and the okay-to-remove status signal, and a flashing light the light pipe for the dispensing status signal.

36. The drug delivery device of claim 35 wherein the LEDs are arranged about the start button in a way that each position of the LEDs also helps the user to interpret a provided signal.

37. The drug delivery device of claim 1 wherein the electronic control unit is further configured to wait after the pressing of the start button for the start button to be pressed again in order to proceed with the drug delivery process.

38. The drug delivery device of claim 37 wherein, if the start button is not pressed by elapse of a wait period, the device automatically powers off.

39. The drug delivery device of claim 1 wherein if the start button is pressed for more longer than a time window during the movement of the plunger from the first position to the second position, the control unit will stop administering the drug and automatically cause the hollow needle to retract and power off.

40. The drug delivery device of claim 39 wherein if the start button is pressed for a duration that falls within the time window, the control unit will temporarily stop administering the drug, and will resume the administering the drug upon the start button being pressed again for a period that again falls within the time window.

41. The drug delivery device of claim 1 further comprising a dedicated panic button which can be used to stop the drug delivery process immediately, retract the hollow needle and have the device power off.

42. The drug delivery device of claim 1 wherein the electronic control unit provides a ready-to start signal via the status indicator and causes the transfer unit to extend the hollow needle and powers the drive unit such that the plunger moves from the first position to the second position if start-up checks provide no errors.

43. The drug delivery device of claim 33 wherein the adhesive layer has a ring portion to facilitate easier removal of the device from the body of the user.

44. The drug delivery device of claim 1 wherein the transfer unit comprises a further sterile barrier to be pierced by the cartridge needle.

* * * * *

UNITED STATES PATENT AND TRADEMARK OFFICE
CERTIFICATE OF CORRECTION

PATENT NO. : 8,303,535 B2
APPLICATION NO. : 13/062957
DATED : November 6, 2012
INVENTOR(S) : Marcel Both et al.

It is certified that error appears in the above-identified patent and that said Letters Patent is hereby corrected as shown below:

In the Claims:

Col. 29, Claim 26, Line 28, "a switch which send" should read --a switch which sends--;

Col. 30, Claim 35, Line 16, "and a flashing light the light pipe" should read --and a flashing light pipe--;

Col. 30, Claim 39, Line 29, "pressed for more longer" should read --pressed for longer--;

Col. 30, Claim 40, Line 37, "will resume the administering" should read
--will resume administering--; and Col. 30, Claim 42, Line 45, "ready-to start signal" should read --ready-to-start signal--.

Signed and Sealed this
Eighth Day of October, 2013

Teresa Stanek Rea
*Deputy Director of the United States Patent and Trademark Office*